United States Patent
Min et al.

(10) Patent No.: US 9,850,512 B2
(45) Date of Patent: Dec. 26, 2017

(54) HYDROLYSIS OF CELLULOSIC FINES IN PRIMARY CLARIFIED SLUDGE OF PAPER MILLS AND THE ADDITION OF A SURFACTANT TO INCREASE THE YIELD

(71) Applicant: The Research Foundation for The State University of New York, Binghamton, NY (US)

(72) Inventors: Byeong Cheol Min, Syracuse, NY (US); Bhavin V. Bhayani, Syracuse, NY (US); Bandaru V. Ramarao, Fayetteville, NY (US)

(73) Assignee: The Research Foundation For The State University of New York, Binghamton, NY (US)

( * ) Notice: Subject to any disclaimer, the term of this patent is extended or adjusted under 35 U.S.C. 154(b) by 0 days.

(21) Appl. No.: 14/212,361

(22) Filed: Mar. 14, 2014

(65) Prior Publication Data

US 2014/0273107 A1  Sep. 18, 2014

Related U.S. Application Data

(60) Provisional application No. 61/792,793, filed on Mar. 15, 2013.

(51) Int. Cl.
*C12P 19/14* (2006.01)
*C12P 19/02* (2006.01)

(52) U.S. Cl.
CPC .............. *C12P 19/14* (2013.01); *C12P 19/02* (2013.01)

(58) Field of Classification Search
CPC ................. C12P 19/14; C12P 19/02
See application file for complete search history.

(56) References Cited

U.S. PATENT DOCUMENTS

| | | |
|---|---|---|
| 3,990,944 A | 11/1976 | Gauss et al. |
| 4,017,642 A | 4/1977 | Orth, Jr. et al. |
| 4,058,411 A | 11/1977 | Bellamy et al. |
| 4,235,968 A | 11/1980 | Pilipski |
| 4,260,685 A | 4/1981 | Pilipski |
| 4,275,163 A | 6/1981 | Gallo |

(Continued)

FOREIGN PATENT DOCUMENTS

WO  WO 2012/112488  *  8/2012

OTHER PUBLICATIONS

Castanon et al., Effects of the Surfactant Tween 80 on Enzymatic Hydrolysis of Newspaper., Biotechnology and Bioengineering (1981), vol. 23, pp. 1365-1372.*

(Continued)

*Primary Examiner* — Alexander Kim
(74) *Attorney, Agent, or Firm* — Steven M. Hoffberg; Tully Rinckey PLLC

(57) ABSTRACT

A method for processing a stream of cellulosic fines containing inorganic particles, to increase a hydrolysis yield of polysaccharide degradation enzymes, such fines in a waste stream from a recycled packaging paper mill to produce a stream of fermentable sugars, comprising treating the fines with a surfactant which selectively binds to the inorganic particles and which reduces binding to the inorganic particles by the polysaccharide degradation enzymes, and degrading polysaccharides in the waste stream with the polysaccharide degradation enzymes.

20 Claims, 2 Drawing Sheets

(56) References Cited

U.S. PATENT DOCUMENTS

| | | |
|---|---|---|
| 4,292,406 A | 9/1981 | Ljungdahl et al. |
| 4,321,278 A | 3/1982 | Johanning et al. |
| 4,321,328 A | 3/1982 | Hoge |
| 4,321,360 A | 3/1982 | Blount |
| 4,431,675 A | 2/1984 | Schroeder et al. |
| 4,540,587 A | 9/1985 | Gajewski |
| 4,594,130 A | 6/1986 | Chang et al. |
| 4,628,029 A | 12/1986 | Eveleigh et al. |
| 4,694,906 A | 9/1987 | Hutchins et al. |
| 4,713,118 A | 12/1987 | Barker et al. |
| 4,831,127 A | 5/1989 | Weibel |
| 4,851,394 A | 7/1989 | Kubodera |
| 4,950,597 A | 8/1990 | Saxena et al. |
| 4,975,459 A | 12/1990 | Mehta et al. |
| 5,023,275 A | 6/1991 | Amick |
| 5,037,663 A | 8/1991 | Dale |
| 5,055,308 A | 10/1991 | Fujinawa et al. |
| 5,059,654 A | 10/1991 | Hou et al. |
| 5,081,026 A | 1/1992 | Heikkila et al. |
| 5,091,399 A | 2/1992 | Osei-Gyimah et al. |
| 5,102,898 A | 4/1992 | Hsu |
| 5,112,382 A | 5/1992 | Hsu |
| 5,118,681 A | 6/1992 | Amick et al. |
| 5,149,524 A | 9/1992 | Sherba et al. |
| 5,151,447 A | 9/1992 | Amick |
| 5,166,390 A | 11/1992 | Weinstein et al. |
| 5,170,620 A | 12/1992 | Whistler et al. |
| 5,171,570 A | 12/1992 | Takemori et al. |
| 5,179,127 A | 1/1993 | Hsu |
| 5,198,074 A | 3/1993 | Villavicencio et al. |
| 5,292,762 A | 3/1994 | Hsu |
| 5,300,672 A | 4/1994 | Weinstein et al. |
| 5,302,592 A | 4/1994 | Osei-Gyimah et al. |
| 5,352,444 A | 10/1994 | Cox et al. |
| 5,391,561 A | 2/1995 | Hsu |
| 5,395,455 A | 3/1995 | Scott et al. |
| 5,395,623 A | 3/1995 | Kovach |
| 5,416,210 A | 5/1995 | Sherba et al. |
| 5,424,202 A | 6/1995 | Ingram et al. |
| 5,424,417 A | 6/1995 | Torget et al. |
| 5,437,992 A | 8/1995 | Bodie et al. |
| 5,458,899 A | 10/1995 | Floyd et al. |
| 5,464,832 A | 11/1995 | Osei-Gyimah et al. |
| 5,487,989 A | 1/1996 | Fowler et al. |
| 5,503,996 A | 4/1996 | Torget et al. |
| 5,505,950 A | 4/1996 | Floyd et al. |
| 5,518,902 A | 5/1996 | Ozaki et al. |
| 5,554,520 A | 9/1996 | Fowler et al. |
| 5,587,157 A | 12/1996 | Cox et al. |
| 5,589,164 A | 12/1996 | Cox et al. |
| 5,683,911 A | 11/1997 | Bodie et al. |
| 5,693,518 A | 12/1997 | Kofod et al. |
| 5,705,369 A | 1/1998 | Torget et al. |
| 5,733,758 A | 3/1998 | Nguyen |
| 5,736,032 A | 4/1998 | Cox et al. |
| 5,747,082 A | 5/1998 | Floyd et al. |
| 5,770,010 A | 6/1998 | Jelks |
| 5,786,313 A | 7/1998 | Schneider et al. |
| 5,792,630 A | 8/1998 | Tonouchi et al. |
| 5,861,271 A | 1/1999 | Fowler et al. |
| 5,863,783 A | 1/1999 | Van Heuvel et al. |
| 5,866,392 A | 2/1999 | Schou et al. |
| 5,871,550 A | 2/1999 | Goedegebuur et al. |
| 5,874,276 A | 2/1999 | Fowler et al. |
| 5,885,819 A | 3/1999 | Kofod et al. |
| 5,888,806 A | 3/1999 | Nguyen |
| 5,908,649 A | 6/1999 | Floyd et al. |
| 5,962,277 A | 10/1999 | Watanabe et al. |
| 5,962,278 A | 10/1999 | Tsuchida et al. |
| 5,989,887 A | 11/1999 | Van Heuvel et al. |
| 6,001,639 A | 12/1999 | Schulein et al. |
| 6,005,141 A | 12/1999 | Schneider et al. |
| 6,008,176 A | 12/1999 | Schneider et al. |
| 6,010,870 A | 1/2000 | Pelzer et al. |
| 6,013,490 A | 1/2000 | Kouda et al. |
| 6,017,740 A | 1/2000 | Kouda et al. |
| 6,048,715 A | 4/2000 | Haynes et al. |
| 6,069,136 A | 5/2000 | Tahara et al. |
| 6,074,856 A | 6/2000 | Wong et al. |
| 6,080,567 A | 6/2000 | Kofod et al. |
| 6,110,712 A | 8/2000 | Tsuchida et al. |
| 6,130,076 A | 10/2000 | Ingram |
| 6,132,998 A | 10/2000 | Naritomi et al. |
| 6,140,105 A | 10/2000 | Watanabe et al. |
| 6,153,413 A | 11/2000 | Watanabe et al. |
| 6,174,700 B1 | 1/2001 | Haynes et al. |
| 6,197,564 B1 | 3/2001 | Kofod et al. |
| 6,207,436 B1 | 3/2001 | Bjornvad et al. |
| 6,228,630 B1 | 5/2001 | Kofod et al. |
| 6,268,196 B1 | 7/2001 | Fowler et al. |
| 6,268,197 B1 | 7/2001 | Schulein et al. |
| 6,309,871 B1 | 10/2001 | Outtrup et al. |
| 6,328,994 B1 | 12/2001 | Shimizu et al. |
| 6,333,181 B1 | 12/2001 | Ingram et al. |
| 6,361,989 B1 | 3/2002 | Svendsen et al. |
| 6,387,690 B1 | 5/2002 | Schulein et al. |
| 6,399,351 B1 | 6/2002 | Bjornvad et al. |
| 6,420,165 B1 | 7/2002 | Weinstein et al. |
| 6,444,653 B1 | 9/2002 | Huppe et al. |
| 6,451,063 B1 | 9/2002 | Clarkson et al. |
| 6,500,658 B1 | 12/2002 | Wu et al. |
| 6,528,298 B1 | 3/2003 | Svendsen et al. |
| 6,555,228 B2 | 4/2003 | Guritza |
| 6,555,335 B1 | 4/2003 | Saloheimo et al. |
| 6,566,114 B1 | 5/2003 | Kauppinen et al. |
| 6,620,605 B2 | 9/2003 | Fowler et al. |
| 6,623,948 B1 | 9/2003 | Outtrup et al. |
| 6,630,340 B2 | 10/2003 | Wilting et al. |
| 6,663,780 B2 | 12/2003 | Heikkila et al. |
| 6,713,460 B2 | 3/2004 | Huppe et al. |
| 6,768,001 B2 | 7/2004 | Saloheimo et al. |
| 6,815,192 B2 | 11/2004 | Schnorr et al. |
| 6,818,434 B2 | 11/2004 | Watanabe et al. |
| 6,855,531 B2 | 2/2005 | Shulein et al. |
| 6,878,199 B2 | 4/2005 | Bowden et al. |
| 6,894,199 B2 | 5/2005 | Heikkila et al. |
| 6,908,995 B2 | 6/2005 | Blount |
| 6,911,565 B2 | 6/2005 | Heikkila et al. |
| 6,942,754 B2 | 9/2005 | Izumi et al. |
| 6,982,159 B2 | 1/2006 | Dunn-Coleman et al. |
| 7,005,289 B2 | 2/2006 | Dunn-Coleman et al. |
| 7,033,811 B2 | 4/2006 | Rey et al. |
| 7,045,331 B2 | 5/2006 | Dunn-Coleman et al. |
| 7,045,332 B2 | 5/2006 | Dunn-Coleman et al. |
| 7,048,952 B2 | 5/2006 | Gerson et al. |
| 7,049,125 B2 | 5/2006 | Dunn-Coleman et al. |
| 7,056,721 B2 | 6/2006 | Dunn-Coleman et al. |
| 7,067,303 B1 | 6/2006 | Nichols et al. |
| 7,070,805 B2 | 7/2006 | Shimizu et al. |
| 7,083,673 B2 | 8/2006 | Bowden et al. |
| 7,109,005 B2 | 9/2006 | Eroma et al. |
| 7,144,716 B2 | 12/2006 | Saville |
| 7,172,891 B2 | 2/2007 | Rey et al. |
| 7,183,093 B2 | 2/2007 | Kauppinen et al. |
| 7,198,925 B2 | 4/2007 | Foody |
| 7,226,772 B2 | 6/2007 | Hseu et al. |
| 7,226,773 B2 | 6/2007 | Schulein et al. |
| 7,273,742 B2 | 9/2007 | Dunn-Coleman et al. |
| 7,320,886 B2 | 1/2008 | Dunn-Coleman et al. |
| 7,344,871 B2 | 3/2008 | Dunn-Coleman et al. |
| 7,344,876 B2 | 3/2008 | Levine |
| 7,351,568 B2 | 4/2008 | Dunn-Coleman et al. |
| 7,351,573 B2 | 4/2008 | Dunn-Coleman et al. |
| 7,361,736 B2 | 4/2008 | Schnorr et al. |
| 7,381,553 B2 | 6/2008 | Zhao et al. |
| 7,399,485 B1 | 7/2008 | Shimizu et al. |
| 7,399,855 B2 | 7/2008 | Frost |
| 7,407,788 B2 | 8/2008 | Dunn-Coleman et al. |
| 7,431,942 B2 | 10/2008 | Shimizu et al. |
| 7,449,319 B2 | 11/2008 | Dunn-Coleman et al. |
| 7,449,550 B2 | 11/2008 | Adney et al. |
| 7,452,707 B2 | 11/2008 | Goedegebuur et al. |
| 7,459,299 B2 | 12/2008 | Goedegebuur et al. |
| 7,503,981 B2 | 3/2009 | Wyman et al. |

(56) References Cited

U.S. PATENT DOCUMENTS

| | | |
|---|---|---|
| 7,504,120 B2 | 3/2009 | Steer et al. |
| 7,527,959 B2 | 5/2009 | Dunn-Coleman et al. |
| 7,547,534 B2 | 6/2009 | Steer et al. |
| 7,566,561 B2 | 7/2009 | Svendsen et al. |
| 7,582,462 B2 | 9/2009 | Dunn-Coleman et al. |
| 7,585,652 B2 | 9/2009 | Foody et al. |
| 7,592,163 B2 | 9/2009 | Zhao et al. |
| 7,592,434 B2 | 9/2009 | Kerovuo et al. |
| 7,601,529 B2 | 10/2009 | Glad et al. |
| 7,611,882 B2 | 11/2009 | Bjornvad et al. |
| 7,625,728 B2 | 12/2009 | Eroma et al. |
| 7,632,479 B2 | 12/2009 | Curren et al. |
| 7,642,079 B2 | 1/2010 | Cayouette et al. |
| 7,651,582 B2 | 1/2010 | Weimer et al. |
| 7,659,099 B2 | 2/2010 | Saville et al. |
| 7,670,813 B2 | 3/2010 | Foody et al. |
| 7,682,811 B2 | 3/2010 | Leschine et al. |
| 7,709,697 B2 | 5/2010 | Raab |
| 7,723,568 B2 | 5/2010 | Lutfiyya et al. |
| 7,727,746 B2 | 6/2010 | Foody et al. |
| 7,727,754 B2 | 6/2010 | Dunn-Coleman et al. |
| 7,732,173 B2 | 6/2010 | Mairal et al. |
| 7,741,089 B2 | 6/2010 | Hitchman et al. |
| 7,754,457 B2 | 7/2010 | Foody et al. |
| 7,781,191 B2 | 8/2010 | Dunson, Jr. et al. |
| 7,785,854 B2 | 8/2010 | St-Pierre et al. |
| 7,786,350 B2 | 8/2010 | Allen et al. |
| 7,786,351 B2 | 8/2010 | Houmard et al. |
| 7,803,601 B2 | 9/2010 | Nobles, Jr. et al. |
| 7,807,419 B2 | 10/2010 | Hennessey et al. |
| 7,807,434 B2 | 10/2010 | Dunn-Coleman et al. |
| 7,810,507 B2 | 10/2010 | Dube et al. |
| 7,811,799 B2 | 10/2010 | Dunn-Coleman et al. |
| 7,816,581 B2 | 10/2010 | Gilbertson et al. |
| 7,819,976 B2 | 10/2010 | Friend et al. |
| 7,829,732 B2 | 11/2010 | Mascal |
| 7,838,666 B2 | 11/2010 | Yaginuma et al. |
| 7,846,705 B2 | 12/2010 | Kensch et al. |
| 7,867,745 B2 | 1/2011 | Hansen et al. |
| 7,875,292 B2 | 1/2011 | Shimizu et al. |
| 7,887,862 B2 | 2/2011 | Paz Briz et al. |
| 7,901,511 B2 | 3/2011 | Griffin et al. |
| 7,906,704 B2 | 3/2011 | Raab |
| 7,910,338 B2 | 3/2011 | Hennessey et al. |
| 7,910,347 B1 | 3/2011 | DiCosimo et al. |
| 7,923,233 B1 | 4/2011 | Dicosimo et al. |
| 7,923,235 B2 | 4/2011 | Foreman et al. |
| 7,923,236 B2 | 4/2011 | Gusakov et al. |
| 7,927,854 B1 | 4/2011 | DiCosimo et al. |
| 7,931,784 B2 | 4/2011 | Medoff |
| 7,932,063 B2 | 4/2011 | Dunson, Jr. et al. |
| 7,932,065 B2 | 4/2011 | Medoff |
| 7,932,072 B1 | 4/2011 | DiCosimo et al. |
| 7,939,488 B2 | 5/2011 | Scheuing et al. |
| 7,943,363 B2 | 5/2011 | Blanchard et al. |
| 7,946,295 B2 | 5/2011 | Brinkley et al. |
| 7,947,813 B2 | 5/2011 | Fahrner et al. |
| 7,951,570 B2 | 5/2011 | Goedegebuur et al. |
| 7,951,571 B2 | 5/2011 | Goedegebuur et al. |
| 7,954,734 B2 | 6/2011 | Hata |
| 7,960,146 B2 | 6/2011 | Dunn-Coleman et al. |
| 7,960,148 B2 | 6/2011 | Steer et al. |
| 7,960,151 B1 | 6/2011 | Dicosimo et al. |
| 7,960,153 B2 | 6/2011 | Czechowski et al. |
| 7,960,160 B2 | 6/2011 | Yaver et al. |
| 7,960,528 B1 | 6/2011 | DiCosimo et al. |
| 7,964,383 B1 | 6/2011 | DiCosimo et al. |
| 7,967,904 B2 | 6/2011 | Bowden et al. |
| 7,972,832 B2 | 7/2011 | Day et al. |
| 7,977,450 B2 | 7/2011 | Frost |
| 7,981,643 B2 | 7/2011 | Dicosimo et al. |
| 7,981,644 B2 | 7/2011 | Dicosimo et al. |
| 7,981,646 B2 | 7/2011 | Heald et al. |
| 7,993,463 B2 | 8/2011 | Griffin et al. |
| 7,993,890 B2 | 8/2011 | Soerensen et al. |
| 7,993,898 B2 | 8/2011 | Andersen et al. |
| 7,998,711 B2 | 8/2011 | Goedegebuur et al. |
| 7,998,713 B2 | 8/2011 | Dunson, Jr. et al. |
| 8,008,056 B2 | 8/2011 | Aehle et al. |
| 8,017,372 B2 | 9/2011 | Andersen et al. |
| 8,017,820 B2 | 9/2011 | Foody et al. |
| 8,030,050 B2 | 10/2011 | Berg et al. |
| 8,034,592 B2 | 10/2011 | Elias et al. |
| 8,043,837 B2 | 10/2011 | Burke et al. |
| 8,043,839 B2 | 10/2011 | Weiner et al. |
| 8,053,566 B2 | 11/2011 | Belanger et al. |
| 8,061,362 B2 | 11/2011 | Mua et al. |
| 8,063,201 B2 | 11/2011 | Medoff |
| 8,067,222 B2 | 11/2011 | Kerovuo et al. |
| 8,071,349 B2 | 12/2011 | Dunn-Coleman et al. |
| 8,071,351 B2 | 12/2011 | Schnorr et al. |
| 8,080,398 B2 | 12/2011 | Holm et al. |
| 8,083,906 B2 | 12/2011 | Medoff |
| 8,092,647 B2 | 1/2012 | Akhtar et al. |
| 8,093,037 B2 | 1/2012 | Picataggio et al. |
| 8,097,442 B2 | 1/2012 | Hitchman et al. |
| 8,097,445 B2 | 1/2012 | Bower et al. |
| 8,101,024 B2 | 1/2012 | Wyman et al. |
| 8,101,393 B2 | 1/2012 | Gray et al. |
| 8,101,398 B2 | 1/2012 | St-Pierre et al. |
| 8,105,398 B2 | 1/2012 | Morgan |
| 8,114,655 B2 | 2/2012 | Dunn-Coleman et al. |
| 8,114,974 B2 | 2/2012 | Picataggio et al. |
| 8,119,385 B2 | 2/2012 | Mathur et al. |
| 8,133,711 B2 | 3/2012 | Dunn-Coleman et al. |
| 8,142,620 B2 | 3/2012 | Medoff |
| 8,143,050 B2 | 3/2012 | Yang et al. |
| 8,143,480 B2 | 3/2012 | Axtell et al. |
| 8,148,133 B2 | 4/2012 | Elias et al. |
| 8,148,579 B2 | 4/2012 | Bradin |
| 8,158,397 B2 | 4/2012 | Jones et al. |
| 8,168,038 B2 | 5/2012 | Medoff |
| 8,173,410 B2 | 5/2012 | Bott et al. |
| 8,178,336 B2 | 5/2012 | Derkx et al. |
| 8,187,860 B2 | 5/2012 | Franklin et al. |
| 8,192,968 B2 | 6/2012 | Edwards et al. |
| 8,202,709 B2 | 6/2012 | Tolan et al. |
| 8,202,831 B2 | 6/2012 | Lant et al. |
| 8,206,963 B2 | 6/2012 | Dicosimo et al. |
| 8,206,964 B2 | 6/2012 | Dicosimo et al. |
| 8,212,087 B2 | 7/2012 | Medoff |
| 8,216,815 B2 | 7/2012 | McDaniel et al. |
| 8,217,227 B2 | 7/2012 | Allen et al. |
| 8,222,010 B2 | 7/2012 | Franklin et al. |
| 8,227,236 B2 | 7/2012 | Picataggio et al. |
| 8,232,080 B2 | 7/2012 | Day et al. |
| 8,236,535 B2 | 8/2012 | Medoff et al. |
| 8,236,542 B2 | 8/2012 | Cascao-Pereira et al. |
| 8,236,546 B2 | 8/2012 | Goedegebuur et al. |
| 8,236,551 B2 | 8/2012 | Dhawan et al. |
| 8,241,461 B1 | 8/2012 | Dyer |
| 8,241,881 B2 | 8/2012 | Bradin |
| 8,247,203 B2 | 8/2012 | Foody et al. |
| 8,247,647 B2 | 8/2012 | Raab |
| 8,257,959 B2 | 9/2012 | Bell et al. |
| 8,263,368 B2 | 9/2012 | Svendsen et al. |
| 8,273,181 B2 | 9/2012 | Foody et al. |
| 8,273,559 B2 | 9/2012 | Geros |
| 8,278,079 B2 | 10/2012 | Dunn-Coleman et al. |
| 8,278,260 B2 | 10/2012 | Saint Victor |
| 8,283,150 B2 | 10/2012 | Adney et al. |
| 8,287,732 B2 | 10/2012 | Chen et al. |
| 8,288,144 B2 | 10/2012 | Glad et al. |
| 8,288,148 B2 | 10/2012 | Cervin et al. |
| 8,293,508 B2 | 10/2012 | Lantero et al. |
| 8,298,795 B2 | 10/2012 | Yang et al. |
| 8,298,799 B2 | 10/2012 | Bornscheuer et al. |
| 8,298,802 B2 | 10/2012 | Dunn-Coleman et al. |
| 8,304,219 B2 | 11/2012 | Levine |
| 8,309,328 B1 | 11/2012 | Dhawan et al. |
| 8,309,331 B2 | 11/2012 | Banerjee et al. |
| 8,317,975 B2 | 11/2012 | Amidon et al. |
| 8,318,461 B2 | 11/2012 | Tolan et al. |
| 8,323,947 B2 | 12/2012 | Yang et al. |

(56) References Cited

U.S. PATENT DOCUMENTS

| | | |
|---|---|---|
| 8,328,947 B2 | 12/2012 | Anand et al. |
| 8,334,430 B2 | 12/2012 | Allen et al. |
| 8,338,139 B2 | 12/2012 | Lali et al. |
| 8,343,747 B2 | 1/2013 | Burke et al. |
| 8,354,263 B2 | 1/2013 | Schnorr et al. |
| 8,357,523 B2 | 1/2013 | Postlethwaite et al. |
| 8,361,762 B2 | 1/2013 | Beck et al. |
| 8,361,767 B2 | 1/2013 | Dunn-Coleman et al. |
| 8,362,322 B2 | 1/2013 | Apuya et al. |
| 8,367,819 B2 | 2/2013 | Frost |
| 8,372,598 B2 | 2/2013 | Mucha |
| 8,377,659 B2 | 2/2013 | Goedegebuur et al. |
| 8,389,254 B2 | 3/2013 | Dicosimo et al. |
| 8,389,255 B2 | 3/2013 | Dicosimo et al. |
| 8,389,256 B2 | 3/2013 | Dicosimo et al. |
| 8,389,257 B2 | 3/2013 | Dicosimo et al. |
| 8,389,258 B2 | 3/2013 | DiCosimo et al. |
| 8,389,259 B2 | 3/2013 | DiCosimo et al. |
| 8,389,260 B2 | 3/2013 | DiCosimo et al. |
| 8,394,616 B2 | 3/2013 | DiCosimo et al. |
| 8,394,617 B2 | 3/2013 | DiCosimo et al. |
| 8,395,023 B2 | 3/2013 | Gilbertson et al. |
| 2001/0010825 A1 | 8/2001 | Shimizu et al. |
| 2001/0044138 A1 | 11/2001 | Watanabe et al. |
| 2002/0012980 A1 | 1/2002 | Sreenath |
| 2002/0045057 A1 | 4/2002 | Guritza |
| 2002/0142034 A1 | 10/2002 | Shimizu et al. |
| 2002/0156048 A1 | 10/2002 | Huppe et al. |
| 2002/0160469 A1 | 10/2002 | Ingram et al. |
| 2002/0164731 A1 | 11/2002 | Eroma et al. |
| 2002/0164774 A1 | 11/2002 | Fowler et al. |
| 2002/0193272 A1 | 12/2002 | Clarkson et al. |
| 2002/0195213 A1 | 12/2002 | Izumi et al. |
| 2003/0013172 A1 | 1/2003 | Gerendash |
| 2003/0022347 A1 | 1/2003 | Sjoholm et al. |
| 2003/0022807 A1 | 1/2003 | Wilting et al. |
| 2003/0032084 A1 | 2/2003 | Saville |
| 2003/0032148 A1 | 2/2003 | Watanabe et al. |
| 2003/0032162 A1 | 2/2003 | Schnorr et al. |
| 2003/0054500 A1 | 3/2003 | Ingram et al. |
| 2003/0054518 A1 | 3/2003 | Saloheimo et al. |
| 2003/0054539 A1 | 3/2003 | Schulein et al. |
| 2003/0082779 A1 | 5/2003 | Dunn-Coleman et al. |
| 2003/0087415 A1 | 5/2003 | Andersen et al. |
| 2003/0092097 A1 | 5/2003 | Andersen et al. |
| 2003/0097029 A1 | 5/2003 | Heikkila et al. |
| 2003/0113732 A1 | 6/2003 | Dunn-Coleman et al. |
| 2003/0113734 A1 | 6/2003 | Dunn-Coleman et al. |
| 2003/0113735 A1 | 6/2003 | Dunn-Coleman et al. |
| 2003/0114330 A1 | 6/2003 | Dunn-Coleman et al. |
| 2003/0119006 A1 | 6/2003 | Dunn-Coleman et al. |
| 2003/0125588 A1 | 7/2003 | Heikkila et al. |
| 2003/0180900 A1 | 9/2003 | Lantero |
| 2003/0203454 A1 | 10/2003 | Chotani et al. |
| 2003/0203466 A1 | 10/2003 | Kauppinen et al. |
| 2003/0211958 A1 | 11/2003 | Svendsen et al. |
| 2003/0216492 A1 | 11/2003 | Bowden et al. |
| 2003/0225005 A1 | 12/2003 | Gerson et al. |
| 2004/0053238 A1 | 3/2004 | Hseu et al. |
| 2004/0067569 A1 | 4/2004 | Rey et al. |
| 2004/0102619 A1 | 5/2004 | Dunn-Coleman et al. |
| 2004/0121436 A1 | 6/2004 | Blount |
| 2004/0157301 A1 | 8/2004 | Chotani et al. |
| 2004/0203134 A1 | 10/2004 | Pyntikov et al. |
| 2004/0210099 A1 | 10/2004 | Shiratori |
| 2004/0231661 A1 | 11/2004 | Griffin et al. |
| 2004/0259218 A1 | 12/2004 | Weimer et al. |
| 2004/0266642 A1 | 12/2004 | Schnorr et al. |
| 2005/0009166 A1 | 1/2005 | Andersen et al. |
| 2005/0037459 A1 | 2/2005 | Goedegebuur et al. |
| 2005/0054039 A1 | 3/2005 | Goedegebuur et al. |
| 2005/0070003 A1 | 3/2005 | Schulein et al. |
| 2005/0075497 A1 | 4/2005 | Utz et al. |
| 2005/0100996 A1 | 5/2005 | Lantero, Jr. et al. |
| 2005/0118130 A1 | 6/2005 | Utz et al. |
| 2005/0120915 A1 | 6/2005 | Bowden et al. |
| 2005/0125860 A1 | 6/2005 | Raab |
| 2005/0129643 A1 | 6/2005 | Lepilleur et al. |
| 2005/0148056 A1 | 7/2005 | Levine |
| 2005/0210548 A1 | 9/2005 | Yaver et al. |
| 2005/0214921 A1 | 9/2005 | Dunn-coleman et al. |
| 2005/0221369 A1 | 10/2005 | Dunn-Coleman et al. |
| 2005/0244878 A1 | 11/2005 | Dunn-Coleman et al. |
| 2005/0244934 A1 | 11/2005 | Foody et al. |
| 2005/0272836 A1 | 12/2005 | Yaginuma et al. |
| 2005/0277172 A1 | 12/2005 | Day et al. |
| 2006/0003433 A1 | 1/2006 | Steer et al. |
| 2006/0018862 A1 | 1/2006 | Chen et al. |
| 2006/0035353 A1 | 2/2006 | Zhao et al. |
| 2006/0046284 A1 | 3/2006 | Dunn-Coleman et al. |
| 2006/0057672 A1 | 3/2006 | Bower et al. |
| 2006/0068475 A1 | 3/2006 | Foody |
| 2006/0084156 A1 | 4/2006 | Lantero et al. |
| 2006/0089283 A1 | 4/2006 | Glad et al. |
| 2006/0104931 A1 | 5/2006 | Fukutome et al. |
| 2006/0110797 A1 | 5/2006 | Rey et al. |
| 2006/0135388 A1 | 6/2006 | Dunn-Coleman et al. |
| 2006/0141601 A1 | 6/2006 | Dunn-Coleman et al. |
| 2006/0154352 A1 | 7/2006 | Foody et al. |
| 2006/0154844 A1 | 7/2006 | Dunn-Coleman et al. |
| 2006/0165613 A1 | 7/2006 | Bjoernvad et al. |
| 2006/0166322 A1 | 7/2006 | Dunn-Coleman et al. |
| 2006/0182802 A1 | 8/2006 | Shimizu et al. |
| 2006/0188965 A1 | 8/2006 | Wyman et al. |
| 2006/0200878 A1 | 9/2006 | Lutfiyya et al. |
| 2006/0205042 A1 | 9/2006 | Aehle et al. |
| 2006/0210971 A1 | 9/2006 | Kerovuo et al. |
| 2006/0211101 A1 | 9/2006 | Chotani et al. |
| 2006/0235115 A1 | 10/2006 | Weimer et al. |
| 2006/0246563 A1 | 11/2006 | Eroma et al. |
| 2006/0255507 A1 | 11/2006 | Bowden et al. |
| 2006/0258554 A1 | 11/2006 | Dunn-Coleman et al. |
| 2006/0259995 A1 | 11/2006 | Cayouette et al. |
| 2006/0275241 A1 | 12/2006 | Padlo et al. |
| 2006/0281157 A1 | 12/2006 | Chotani et al. |
| 2007/0011775 A1 | 1/2007 | Allen et al. |
| 2007/0031918 A1 | 2/2007 | Dunson, Jr. et al. |
| 2007/0031919 A1 | 2/2007 | Dunson, Jr. et al. |
| 2007/0031953 A1 | 2/2007 | Dunson, Jr. et al. |
| 2007/0031954 A1 | 2/2007 | Mairal et al. |
| 2007/0036832 A1 | 2/2007 | Williams et al. |
| 2007/0037259 A1 | 2/2007 | Hennessey et al. |
| 2007/0059813 A1 | 3/2007 | Saville |
| 2007/0072185 A1 | 3/2007 | Schnorr et al. |
| 2007/0079944 A1 | 4/2007 | Amidon et al. |
| 2007/0083947 A1 | 4/2007 | Huang et al. |
| 2007/0083949 A1 | 4/2007 | Huang et al. |
| 2007/0083950 A1 | 4/2007 | Huang et al. |
| 2007/0083951 A1 | 4/2007 | Huang et al. |
| 2007/0083952 A1 | 4/2007 | Huang et al. |
| 2007/0087066 A1 | 4/2007 | Gerson et al. |
| 2007/0089184 A1 | 4/2007 | Huang et al. |
| 2007/0089185 A1 | 4/2007 | Huang et al. |
| 2007/0089186 A1 | 4/2007 | Huang et al. |
| 2007/0089187 A1 | 4/2007 | Huang et al. |
| 2007/0089188 A1 | 4/2007 | Huang et al. |
| 2007/0089189 A1 | 4/2007 | Huang et al. |
| 2007/0089190 A1 | 4/2007 | Huang et al. |
| 2007/0089191 A1 | 4/2007 | Huang et al. |
| 2007/0089192 A1 | 4/2007 | Huang et al. |
| 2007/0089193 A1 | 4/2007 | Huang et al. |
| 2007/0089194 A1 | 4/2007 | Huang et al. |
| 2007/0089195 A1 | 4/2007 | Huang et al. |
| 2007/0089196 A1 | 4/2007 | Huang et al. |
| 2007/0092934 A1 | 4/2007 | Jones et al. |
| 2007/0092935 A1 | 4/2007 | Jones et al. |
| 2007/0094748 A1 | 4/2007 | Huang et al. |
| 2007/0105112 A1 | 5/2007 | Hitchman et al. |
| 2007/0113301 A1 | 5/2007 | Huang et al. |
| 2007/0113302 A1 | 5/2007 | Huang et al. |
| 2007/0118917 A1 | 5/2007 | Huang et al. |
| 2007/0118918 A1 | 5/2007 | Huang et al. |
| 2007/0141660 A1 | 6/2007 | Chotani et al. |
| 2007/0141693 A1 | 6/2007 | Berg et al. |

(56) References Cited

U.S. PATENT DOCUMENTS

| | | |
|---|---|---|
| 2007/0148730 A1 | 6/2007 | Adney |
| 2007/0148751 A1 | 6/2007 | Griffin et al. |
| 2007/0149777 A1 | 6/2007 | Frost |
| 2007/0172916 A1 | 7/2007 | Jones et al. |
| 2007/0173431 A1 | 7/2007 | Day et al. |
| 2007/0175825 A1 | 8/2007 | Denney |
| 2007/0178569 A1 | 8/2007 | Leschine et al. |
| 2007/0192903 A1 | 8/2007 | Heck et al. |
| 2007/0199095 A1 | 8/2007 | Allen et al. |
| 2007/0199903 A1 | 8/2007 | Denney |
| 2007/0202566 A1 | 8/2007 | Bornscheuer et al. |
| 2007/0207530 A1 | 9/2007 | Dunn-Coleman et al. |
| 2007/0207939 A1 | 9/2007 | Fenyvesi et al. |
| 2007/0213249 A1 | 9/2007 | Dunn-Coleman et al. |
| 2007/0218541 A1 | 9/2007 | Denney et al. |
| 2007/0219521 A1 | 9/2007 | Hird et al. |
| 2007/0221552 A1 | 9/2007 | Denney |
| 2007/0227971 A1 | 10/2007 | Denney |
| 2007/0241306 A1 | 10/2007 | Wehner et al. |
| 2007/0254031 A1 | 11/2007 | Shimizu et al. |
| 2007/0298475 A1 | 12/2007 | Heald et al. |
| 2008/0009047 A1 | 1/2008 | Bell et al. |
| 2008/0020435 A1 | 1/2008 | Burke et al. |
| 2008/0029110 A1 | 2/2008 | Dube et al. |
| 2008/0034453 A1 | 2/2008 | Cheikh et al. |
| 2008/0056983 A1 | 3/2008 | Curren et al. |
| 2008/0064064 A1 | 3/2008 | Kensch et al. |
| 2008/0064906 A1 | 3/2008 | Foody et al. |
| 2008/0070291 A1 | 3/2008 | Lam et al. |
| 2008/0076152 A1 | 3/2008 | St-Pierre et al. |
| 2008/0076314 A1 | 3/2008 | Blanz et al. |
| 2008/0085520 A1 | 4/2008 | Nobles, Jr. et al. |
| 2008/0085536 A1 | 4/2008 | Nobles, Jr. et al. |
| 2008/0095889 A1 | 4/2008 | Dunn-Coleman et al. |
| 2008/0102502 A1 | 5/2008 | Foody et al. |
| 2008/0113413 A1 | 5/2008 | Nobles et al. |
| 2008/0138880 A1 | 6/2008 | Schnorr et al. |
| 2008/0145912 A1 | 6/2008 | Schulein et al. |
| 2008/0176282 A1 | 7/2008 | Dunn-Coleman et al. |
| 2008/0193981 A1 | 8/2008 | Fahrner et al. |
| 2008/0193992 A1 | 8/2008 | Levine |
| 2008/0201801 A1 | 8/2008 | Allen et al. |
| 2008/0202684 A1 | 8/2008 | Weimer et al. |
| 2008/0206836 A1 | 8/2008 | Andersen et al. |
| 2008/0227161 A1 | 9/2008 | Levie et al. |
| 2008/0227173 A1 | 9/2008 | Berg et al. |
| 2008/0227182 A1 | 9/2008 | Anderson et al. |
| 2008/0229456 A1 | 9/2008 | Huang et al. |
| 2008/0229657 A1 | 9/2008 | Senyk et al. |
| 2008/0233175 A1 | 9/2008 | Steer et al. |
| 2008/0241900 A1 | 10/2008 | Zhao et al. |
| 2008/0248160 A1 | 10/2008 | Steer et al. |
| 2008/0251374 A1 | 10/2008 | McManigal |
| 2008/0254080 A1 | 10/2008 | Glynson et al. |
| 2008/0261267 A1 | 10/2008 | Ferrer et al. |
| 2008/0274527 A1 | 11/2008 | Soerensen et al. |
| 2008/0292701 A1 | 11/2008 | Shimizu et al. |
| 2008/0292747 A1 | 11/2008 | Berg et al. |
| 2008/0293086 A1 | 11/2008 | Contag |
| 2008/0293114 A1 | 11/2008 | Foody et al. |
| 2008/0305531 A1 | 12/2008 | Lam et al. |
| 2008/0311640 A1 | 12/2008 | Cox et al. |
| 2009/0004714 A1 | 1/2009 | Norholm et al. |
| 2009/0004726 A1 | 1/2009 | Liu |
| 2009/0005532 A1 | 1/2009 | Frost |
| 2009/0013434 A1 | 1/2009 | Huang et al. |
| 2009/0017512 A1 | 1/2009 | May et al. |
| 2009/0025738 A1 | 1/2009 | Mua et al. |
| 2009/0025739 A1 | 1/2009 | Brinkley et al. |
| 2009/0035826 A1 | 2/2009 | Tolan et al. |
| 2009/0036648 A1 | 2/2009 | Dunn-Coleman et al. |
| 2009/0038023 A1 | 2/2009 | Weiner et al. |
| 2009/0042259 A1 | 2/2009 | Dale et al. |
| 2009/0042266 A1 | 2/2009 | Vehmaanpera et al. |
| 2009/0050134 A1 | 2/2009 | Friend et al. |
| 2009/0053777 A1 | 2/2009 | Hennessey et al. |
| 2009/0053800 A1 | 2/2009 | Friend et al. |
| 2009/0056201 A1 | 3/2009 | Morgan |
| 2009/0056707 A1 | 3/2009 | Foody et al. |
| 2009/0061490 A1 | 3/2009 | Edwards et al. |
| 2009/0068714 A1 | 3/2009 | Leschine et al. |
| 2009/0070898 A1 | 3/2009 | Allen et al. |
| 2009/0075336 A1 | 3/2009 | Goedegebuur et al. |
| 2009/0081762 A1 | 3/2009 | Adney et al. |
| 2009/0093028 A1 | 4/2009 | Doran Peterson et al. |
| 2009/0098266 A1 | 4/2009 | Briz et al. |
| 2009/0099079 A1 | 4/2009 | Emalfarb et al. |
| 2009/0136476 A1 | 5/2009 | Soerensen et al. |
| 2009/0137438 A1 | 5/2009 | Lepilleur et al. |
| 2009/0142848 A1 | 6/2009 | Wyman et al. |
| 2009/0155238 A1 | 6/2009 | Weiner et al. |
| 2009/0163397 A1 | 6/2009 | Goedegebuur et al. |
| 2009/0170174 A1 | 7/2009 | Czechowski et al. |
| 2009/0170181 A1 | 7/2009 | Dunn-Coleman et al. |
| 2009/0170747 A1 | 7/2009 | Andersen et al. |
| 2009/0172838 A1 | 7/2009 | Axtell et al. |
| 2009/0176292 A1 | 7/2009 | Dunn-Coleman et al. |
| 2009/0181126 A1 | 7/2009 | Wicking et al. |
| 2009/0181433 A1 | 7/2009 | Chotani et al. |
| 2009/0194243 A1 | 8/2009 | Akhtar et al. |
| 2009/0198046 A1 | 8/2009 | Fanselow et al. |
| 2009/0202675 A1 | 8/2009 | Derkx et al. |
| 2009/0203102 A1 | 8/2009 | Cervin et al. |
| 2009/0209009 A1 | 8/2009 | Tolan et al. |
| 2009/0217569 A1 | 9/2009 | Pastinen et al. |
| 2009/0220480 A1 | 9/2009 | Gray et al. |
| 2009/0221051 A1 | 9/2009 | Steer et al. |
| 2009/0224086 A1 | 9/2009 | Hata |
| 2009/0226979 A1 | 9/2009 | Retsina et al. |
| 2009/0233335 A1 | 9/2009 | Goedegebuur et al. |
| 2009/0234142 A1 | 9/2009 | Mascal |
| 2009/0235388 A1 | 9/2009 | Allen et al. |
| 2009/0247448 A1 | 10/2009 | Glad et al. |
| 2009/0258172 A1 | 10/2009 | Bowden et al. |
| 2009/0280105 A1 | 11/2009 | Gusakov et al. |
| 2009/0286294 A1 | 11/2009 | Blanchard et al. |
| 2009/0286295 A1 | 11/2009 | Medoff et al. |
| 2009/0297495 A1 | 12/2009 | Kerovuo et al. |
| 2009/0298149 A1 | 12/2009 | Wang et al. |
| 2009/0311752 A1 | 12/2009 | Bodie et al. |
| 2009/0312221 A1 | 12/2009 | Lant et al. |
| 2009/0312537 A1 | 12/2009 | Medoff |
| 2009/0317864 A1 | 12/2009 | Svendsen et al. |
| 2009/0318571 A1 | 12/2009 | Utz et al. |
| 2009/0324574 A1 | 12/2009 | Mathur et al. |
| 2009/0325254 A1 | 12/2009 | Zhao et al. |
| 2010/0003234 A1 | 1/2010 | Blum et al. |
| 2010/0003716 A1 | 1/2010 | Cervin et al. |
| 2010/0003733 A1 | 1/2010 | Foody et al. |
| 2010/0011456 A1 | 1/2010 | Mathur et al. |
| 2010/0021988 A1 | 1/2010 | Kerovuo et al. |
| 2010/0028966 A1 | 2/2010 | Blanchard et al. |
| 2010/0031398 A1 | 2/2010 | Lewis et al. |
| 2010/0035320 A1 | 2/2010 | Blanchard et al. |
| 2010/0041104 A1 | 2/2010 | Cascao-Pereira et al. |
| 2010/0048417 A1 | 2/2010 | Jones et al. |
| 2010/0048964 A1 | 2/2010 | Calabria et al. |
| 2010/0055747 A1 | 3/2010 | Kelemen et al. |
| 2010/0055753 A1 | 3/2010 | Geros |
| 2010/0056774 A1 | 3/2010 | Anand et al. |
| 2010/0068768 A1 | 3/2010 | Tolan et al. |
| 2010/0068790 A1 | 3/2010 | Bell et al. |
| 2010/0071259 A1 | 3/2010 | Hu et al. |
| 2010/0075404 A1 | 3/2010 | Templeton |
| 2010/0086978 A1 | 4/2010 | Beck et al. |
| 2010/0087687 A1 | 4/2010 | Medoff |
| 2010/0095390 A1 | 4/2010 | Weiner et al. |
| 2010/0099640 A1 | 4/2010 | Geuns et al. |
| 2010/0101605 A1 | 4/2010 | Saint Victor |
| 2010/0105114 A1 | 4/2010 | Blanchard et al. |
| 2010/0107342 A1 | 5/2010 | Schulein et al. |
| 2010/0108567 A1 | 5/2010 | Medoff |
| 2010/0112242 A1 | 5/2010 | Medoff |
| 2010/0113846 A1 | 5/2010 | McAuliffe et al. |

(56) References Cited

U.S. PATENT DOCUMENTS

| | | |
|---|---|---|
| 2010/0124583 A1 | 5/2010 | Medoff |
| 2010/0129835 A1 | 5/2010 | Bodie |
| 2010/0136113 A1 | 6/2010 | Steer et al. |
| 2010/0136661 A1 | 6/2010 | Leschine et al. |
| 2010/0137647 A1 | 6/2010 | Bradin |
| 2010/0143998 A1 | 6/2010 | Leschine et al. |
| 2010/0144584 A1 | 6/2010 | Saint Victor |
| 2010/0151546 A1 | 6/2010 | Leschine et al. |
| 2010/0151547 A1 | 6/2010 | Platz |
| 2010/0151551 A1 | 6/2010 | Leschine et al. |
| 2010/0159510 A1 | 6/2010 | Raab |
| 2010/0159553 A1 | 6/2010 | Bradin |
| 2010/0159566 A1 | 6/2010 | Leschine et al. |
| 2010/0160201 A1 | 6/2010 | Scheuing et al. |
| 2010/0167370 A1 | 7/2010 | Chotani et al. |
| 2010/0167371 A1 | 7/2010 | Chotani et al. |
| 2010/0179315 A1 | 7/2010 | Medoff |
| 2010/0184175 A1 | 7/2010 | Dunn-Coleman et al. |
| 2010/0184178 A1 | 7/2010 | Beck et al. |
| 2010/0189706 A1 | 7/2010 | Chang et al. |
| 2010/0196977 A1 | 8/2010 | Chotani et al. |
| 2010/0196978 A1 | 8/2010 | Wood et al. |
| 2010/0196981 A1 | 8/2010 | Aharon et al. |
| 2010/0199548 A1 | 8/2010 | del Cardayre et al. |
| 2010/0212091 A1 | 8/2010 | Schnorr et al. |
| 2010/0216200 A1 | 8/2010 | Leschine et al. |
| 2010/0221784 A1 | 9/2010 | Fujdala et al. |
| 2010/0221819 A1 | 9/2010 | Foody et al. |
| 2010/0223694 A1 | 9/2010 | Lutfiyya et al. |
| 2010/0240128 A1 | 9/2010 | Fillatti et al. |
| 2010/0263264 A1 | 10/2010 | Augier et al. |
| 2010/0267110 A1 | 10/2010 | Hitchman et al. |
| 2010/0268000 A1 | 10/2010 | Parekh et al. |
| 2010/0273214 A1 | 10/2010 | Holm et al. |
| 2010/0279354 A1 | 11/2010 | de Crecy |
| 2010/0279361 A1 | 11/2010 | South et al. |
| 2010/0285534 A1 | 11/2010 | South et al. |
| 2010/0287826 A1 | 11/2010 | Hoffman et al. |
| 2010/0291653 A1 | 11/2010 | Ness et al. |
| 2010/0297704 A1 | 11/2010 | Li |
| 2010/0297721 A1 | 11/2010 | Hogsett et al. |
| 2010/0298612 A1 | 11/2010 | Behrouzian et al. |
| 2010/0304420 A1 | 12/2010 | Gray |
| 2010/0304439 A1 | 12/2010 | Medoff |
| 2010/0304440 A1 | 12/2010 | Medoff |
| 2010/0312028 A1 | 12/2010 | Olson et al. |
| 2010/0317059 A1 | 12/2010 | Postlethwaite et al. |
| 2010/0317087 A1 | 12/2010 | St-Pierre et al. |
| 2010/0319862 A1 | 12/2010 | Rahman |
| 2010/0330633 A1 | 12/2010 | Walther et al. |
| 2011/0000125 A1 | 1/2011 | McDaniel et al. |
| 2011/0003341 A1 | 1/2011 | Nojiri et al. |
| 2011/0003345 A1 | 1/2011 | Nobles, Jr. et al. |
| 2011/0014672 A1 | 1/2011 | Chotani et al. |
| 2011/0016545 A1 | 1/2011 | Gray et al. |
| 2011/0020874 A1 | 1/2011 | Hata |
| 2011/0027346 A1 | 2/2011 | Weiner et al. |
| 2011/0027837 A1 | 2/2011 | Medoff |
| 2011/0028672 A1 | 2/2011 | Dahlman et al. |
| 2011/0033391 A1 | 2/2011 | Weiner et al. |
| 2011/0035838 A1 | 2/2011 | Lutfiyya et al. |
| 2011/0035839 A1 | 2/2011 | Lutfiyya et al. |
| 2011/0039308 A1 | 2/2011 | Slupska et al. |
| 2011/0039309 A1 | 2/2011 | Conner et al. |
| 2011/0039317 A1 | 2/2011 | Medoff |
| 2011/0039318 A1 | 2/2011 | Lehr |
| 2011/0039320 A1 | 2/2011 | Li et al. |
| 2011/0040058 A1 | 2/2011 | McAuliffe et al. |
| 2011/0045544 A1 | 2/2011 | Vehmaanpera et al. |
| 2011/0046422 A1 | 2/2011 | McAuliffe et al. |
| 2011/0053245 A1 | 3/2011 | Weiner et al. |
| 2011/0061666 A1 | 3/2011 | Dube et al. |
| 2011/0065910 A1 | 3/2011 | Medoff |
| 2011/0076743 A1 | 3/2011 | Beck et al. |
| 2011/0081335 A1 | 4/2011 | Medoff |
| 2011/0081336 A1 | 4/2011 | Medoff |
| 2011/0081412 A1 | 4/2011 | Shimizu et al. |
| 2011/0081697 A1 | 4/2011 | Liu |
| 2011/0086408 A1 | 4/2011 | Power et al. |
| 2011/0086410 A1 | 4/2011 | Dunn-Coleman et al. |
| 2011/0091940 A1 | 4/2011 | Atalla |
| 2011/0091950 A1 | 4/2011 | Hansen et al. |
| 2011/0093965 A1 | 4/2011 | O'Donoghue et al. |
| 2011/0095111 A1 | 4/2011 | Briz et al. |
| 2011/0097786 A1 | 4/2011 | Howard et al. |
| 2011/0100359 A1 | 5/2011 | North |
| 2011/0111456 A1 | 5/2011 | Medoff |
| 2011/0117067 A1 | 5/2011 | Esteghlalian et al. |
| 2011/0117619 A1 | 5/2011 | Hansen et al. |
| 2011/0124058 A1 | 5/2011 | Baidyaroy et al. |
| 2011/0124074 A1 | 5/2011 | Den Haan et al. |
| 2011/0125118 A1 | 5/2011 | Lynch |
| 2011/0129880 A1 | 6/2011 | Conners et al. |
| 2011/0129881 A1 | 6/2011 | Yang et al. |
| 2011/0129886 A1 | 6/2011 | Howard et al. |
| 2011/0129887 A1 | 6/2011 | Contag et al. |
| 2011/0130488 A1 | 6/2011 | Yoshino et al. |
| 2011/0136174 A1 | 6/2011 | Kosugi et al. |
| 2011/0136196 A1 | 6/2011 | Elias et al. |
| 2011/0136907 A1 | 6/2011 | DiCosimo et al. |
| 2011/0136908 A1 | 6/2011 | DiCosimo et al. |
| 2011/0138502 A1 | 6/2011 | Raab |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0143398 A1 | 6/2011 | Howard et al. |
| 2011/0144241 A1 | 6/2011 | Yoshino et al. |
| 2011/0146138 A1 | 6/2011 | Berry et al. |
| 2011/0146142 A1 | 6/2011 | Lee et al. |
| 2011/0150857 A1 | 6/2011 | Dicosimo et al. |
| 2011/0152368 A1 | 6/2011 | Dicosimo et al. |
| 2011/0152369 A1 | 6/2011 | Dicosimo et al. |
| 2011/0152370 A1 | 6/2011 | Dicosimo et al. |
| 2011/0152812 A1 | 6/2011 | Hird et al. |
| 2011/0155559 A1 | 6/2011 | Medoff |
| 2011/0159544 A1 | 6/2011 | Puranen et al. |
| 2011/0165660 A1 | 7/2011 | Picataggio et al. |
| 2011/0165661 A1 | 7/2011 | Picataggio et al. |
| 2011/0171705 A1 | 7/2011 | Kotlar et al. |
| 2011/0171709 A1 | 7/2011 | Bardsley |
| 2011/0177561 A1 | 7/2011 | Goedegebuur et al. |
| 2011/0177565 A1 | 7/2011 | Cho et al. |
| 2011/0177573 A1 | 7/2011 | All et al. |
| 2011/0178261 A1 | 7/2011 | Feher et al. |
| 2011/0183379 A1 | 7/2011 | Ladisch et al. |
| 2011/0183396 A1 | 7/2011 | Noda et al. |
| 2011/0185456 A1 | 7/2011 | Cheikh et al. |
| 2011/0190488 A1 | 8/2011 | Wicks |
| 2011/0195481 A1 | 8/2011 | Svendsen et al. |
| 2011/0201093 A1 | 8/2011 | Czechowski et al. |
| 2011/0207192 A1 | 8/2011 | Pigeau et al. |
| 2011/0212499 A1 | 9/2011 | Ladisch et al. |
| 2011/0212505 A1 | 9/2011 | Dunn-Coleman et al. |
| 2011/0224416 A1 | 9/2011 | Picataggio et al. |
| 2011/0229956 A1 | 9/2011 | Day et al. |
| 2011/0229959 A1 | 9/2011 | Picataggio et al. |
| 2011/0232160 A1 | 9/2011 | Siskin et al. |
| 2011/0232161 A1 | 9/2011 | Siskin et al. |
| 2011/0232162 A1 | 9/2011 | Siskin et al. |
| 2011/0232163 A1 | 9/2011 | Siskin et al. |
| 2011/0232164 A1 | 9/2011 | Siskin et al. |
| 2011/0233042 A1 | 9/2011 | Siskin et al. |
| 2011/0236335 A1 | 9/2011 | Dicosimo et al. |
| 2011/0236336 A1 | 9/2011 | Dicosimo et al. |
| 2011/0236337 A1 | 9/2011 | Dicosimo et al. |
| 2011/0236338 A1 | 9/2011 | Dicosimo et al. |
| 2011/0236339 A1 | 9/2011 | Dicosimo et al. |
| 2011/0237769 A1 | 9/2011 | Feher et al. |
| 2011/0239333 A1 | 9/2011 | Yaver et al. |
| 2011/0250635 A1 | 10/2011 | Paz Briz et al. |
| 2011/0250638 A1 | 10/2011 | Sjoede et al. |
| 2011/0250646 A1 | 10/2011 | Bazzana et al. |
| 2011/0250667 A1 | 10/2011 | Elias et al. |

(56) References Cited

U.S. PATENT DOCUMENTS

| | | |
|---|---|---|
| 2011/0250674 A1 | 10/2011 | Andersen et al. |
| 2011/0251377 A1 | 10/2011 | Rahman et al. |
| 2011/0262984 A1 | 10/2011 | Nguyen |
| 2011/0262985 A1 | 10/2011 | Medoff |
| 2011/0268858 A1 | 11/2011 | Heald et al. |
| 2011/0269201 A1 | 11/2011 | Gray et al. |
| 2011/0271875 A1 | 11/2011 | Ahmed et al. |
| 2011/0275118 A1 | 11/2011 | De Crecy |
| 2011/0275130 A1 | 11/2011 | Pronk et al. |
| 2011/0294164 A1 | 12/2011 | Goedegebuur et al. |
| 2011/0294165 A1 | 12/2011 | Goedegebuur et al. |
| 2011/0294181 A1 | 12/2011 | Weydahl |
| 2011/0296543 A1 | 12/2011 | Chang et al. |
| 2011/0296555 A1 | 12/2011 | Ivashuta et al. |
| 2011/0300585 A1 | 12/2011 | Banerjee et al. |
| 2011/0300586 A1 | 12/2011 | Liu et al. |
| 2011/0306083 A1 | 12/2011 | Mucha |
| 2011/0306100 A1 | 12/2011 | De Crecy |
| 2011/0306101 A1 | 12/2011 | De Crecy |
| 2011/0306117 A1 | 12/2011 | Lam et al. |
| 2011/0312048 A1 | 12/2011 | Fanselow et al. |
| 2011/0312055 A1 | 12/2011 | Weydahl |
| 2011/0312058 A1 | 12/2011 | Sibbesen et al. |
| 2011/0314726 A1 | 12/2011 | Jameel et al. |
| 2011/0315154 A1 | 12/2011 | Mua et al. |
| 2011/0318796 A1 | 12/2011 | Walther |
| 2011/0318798 A1 | 12/2011 | Walther et al. |
| 2011/0319849 A1 | 12/2011 | Collias et al. |
| 2012/0003701 A1 | 1/2012 | Brevnova et al. |
| 2012/0003703 A1 | 1/2012 | Mitchell et al. |
| 2012/0003704 A1 | 1/2012 | Medoff |
| 2012/0005949 A1 | 1/2012 | Stevens et al. |
| 2012/0006320 A1 | 1/2012 | Nguyen |
| 2012/0009631 A1 | 1/2012 | Yang et al. |
| 2012/0009634 A1 | 1/2012 | Burke et al. |
| 2012/0009640 A1 | 1/2012 | Behrouzian et al. |
| 2012/0010436 A1 | 1/2012 | Lee et al. |
| 2012/0010437 A1 | 1/2012 | Jevtic et al. |
| 2012/0010438 A1 | 1/2012 | Lee et al. |
| 2012/0010439 A1 | 1/2012 | Jevtic et al. |
| 2012/0010440 A1 | 1/2012 | Sarager et al. |
| 2012/0010443 A1 | 1/2012 | Jevtic et al. |
| 2012/0010444 A1 | 1/2012 | Horton et al. |
| 2012/0010445 A1 | 1/2012 | Johnston et al. |
| 2012/0010446 A1 | 1/2012 | Warner et al. |
| 2012/0010447 A1 | 1/2012 | Warner et al. |
| 2012/0010448 A1 | 1/2012 | Sarager et al. |
| 2012/0015408 A1 | 1/2012 | Baidyaroy et al. |
| 2012/0015422 A1 | 1/2012 | Huang et al. |
| 2012/0021092 A1 | 1/2012 | Sibbesen et al. |
| 2012/0021490 A1 | 1/2012 | Steer et al. |
| 2012/0028306 A1 | 2/2012 | Sibbesen et al. |
| 2012/0028325 A1 | 2/2012 | Herring et al. |
| 2012/0029247 A1 | 2/2012 | Holbrey et al. |
| 2012/0030838 A1 | 2/2012 | Gusakov et al. |
| 2012/0035400 A1 | 2/2012 | Johnston et al. |
| 2012/0036599 A1 | 2/2012 | Gusakov et al. |
| 2012/0036768 A1 | 2/2012 | Phillips et al. |
| 2012/0036769 A1 | 2/2012 | Johnston et al. |
| 2012/0040409 A1 | 2/2012 | Hau et al. |
| 2012/0040435 A1 | 2/2012 | Aehle et al. |
| 2012/0041075 A1 | 2/2012 | Johnston et al. |
| 2012/0045811 A1 | 2/2012 | Dunn-Coleman et al. |
| 2012/0045812 A1 | 2/2012 | Bergsma et al. |
| 2012/0046501 A1 | 2/2012 | Warner et al. |
| 2012/0052534 A1 | 3/2012 | Harlick et al. |
| 2012/0059197 A1 | 3/2012 | Jevtic et al. |
| 2012/0064579 A1 | 3/2012 | Kelley et al. |
| 2012/0064592 A1 | 3/2012 | O'Mullan et al. |
| 2012/0064609 A1 | 3/2012 | Clement et al. |
| 2012/0066781 A1 | 3/2012 | Weiner et al. |
| 2012/0077216 A1 | 3/2012 | Zhang et al. |
| 2012/0077247 A1 | 3/2012 | Medoff |
| 2012/0079665 A1 | 4/2012 | Schnorr et al. |
| 2012/0083019 A1 | 4/2012 | Baidyaroy et al. |
| 2012/0094340 A1 | 4/2012 | Morgan |
| 2012/0094343 A1 | 4/2012 | Hogsett et al. |
| 2012/0094355 A1 | 4/2012 | Medoff |
| 2012/0094358 A1 | 4/2012 | Medoff |
| 2012/0097194 A1 | 4/2012 | McDaniel et al. |
| 2012/0100045 A1 | 4/2012 | Beldring et al. |
| 2012/0100587 A1 | 4/2012 | Dunn-Coleman et al. |
| 2012/0101250 A1 | 4/2012 | Sakuma et al. |
| 2012/0107880 A1 | 5/2012 | Baidyaroy et al. |
| 2012/0107881 A1 | 5/2012 | Dhawan et al. |
| 2012/0107887 A1 | 5/2012 | Chheda et al. |
| 2012/0107888 A1 | 5/2012 | Schmalisch et al. |
| 2012/0107892 A1 | 5/2012 | Agbogbo et al. |
| 2012/0108798 A1 | 5/2012 | Wenger et al. |
| 2012/0111321 A1 | 5/2012 | Nguyen et al. |
| 2012/0115192 A1 | 5/2012 | Lali et al. |
| 2012/0129229 A1 | 5/2012 | McBride et al. |
| 2012/0129696 A1 | 5/2012 | Kohle et al. |
| 2012/0135489 A1 | 5/2012 | Weydahl |
| 2012/0135499 A1 | 5/2012 | Bower et al. |
| 2012/0135500 A1 | 5/2012 | Aehle et al. |
| 2012/0142046 A1 | 6/2012 | McBride et al. |
| 2012/0142065 A1 | 6/2012 | Medoff |
| 2012/0142068 A1 | 6/2012 | Medoff |
| 2012/0142886 A1 | 6/2012 | Frost |
| 2012/0146468 A1 | 6/2012 | Uehira et al. |
| 2012/0149065 A1 | 6/2012 | DaCunha et al. |
| 2012/0149077 A1 | 6/2012 | Shaw, IV et al. |
| 2012/0149949 A1 | 6/2012 | Weiner et al. |
| 2012/0151827 A1 | 6/2012 | Powell et al. |
| 2012/0156155 A1 | 6/2012 | Dicosimo et al. |
| 2012/0156156 A1 | 6/2012 | Dicosimo et al. |
| 2012/0156157 A1 | 6/2012 | DiCosimo et al. |
| 2012/0156158 A1 | 6/2012 | DiCosimo et al. |
| 2012/0156159 A1 | 6/2012 | DiCosimo et al. |
| 2012/0156160 A1 | 6/2012 | DiCosimo et al. |
| 2012/0156161 A1 | 6/2012 | DiCosimo et al. |
| 2012/0156162 A1 | 6/2012 | DiCosimo et al. |
| 2012/0156741 A1 | 6/2012 | Chheda et al. |
| 2012/0156754 A1 | 6/2012 | Dhawan et al. |
| 2012/0157721 A1 | 6/2012 | Weiner et al. |
| 2012/0157725 A1 | 6/2012 | McAuliffe |
| 2012/0159839 A1 | 6/2012 | Koskinen et al. |
| 2012/0159840 A1 | 6/2012 | Koskinen et al. |
| 2012/0164696 A1 | 6/2012 | Yang et al. |
| 2012/0164709 A1 | 6/2012 | Yang et al. |
| 2012/0165517 A1 | 6/2012 | Uehira et al. |
| 2012/0165562 A1 | 6/2012 | Hattendorf et al. |
| 2012/0171732 A1 | 7/2012 | Norholm et al. |
| 2012/0178975 A1 | 7/2012 | Weiner et al. |
| 2012/0184007 A1 | 7/2012 | Picataggio et al. |
| 2012/0184020 A1 | 7/2012 | Picataggio et al. |
| 2012/0190054 A1 | 7/2012 | Malten et al. |
| 2012/0190076 A1 | 7/2012 | Clark et al. |
| 2012/0190840 A1 | 7/2012 | Weydahl |
| 2012/0196338 A1 | 8/2012 | Blanchard et al. |
| 2012/0199298 A1 | 8/2012 | Dyer |
| 2012/0199299 A1 | 8/2012 | Dyer |
| 2012/0208235 A1 | 8/2012 | Zhang et al. |
| 2012/0209034 A1 | 8/2012 | Zhou et al. |
| 2012/0210467 A1 | 8/2012 | Barton et al. |
| 2012/0211184 A1 | 8/2012 | Jemaa et al. |
| 2012/0214209 A1 | 8/2012 | Chotani et al. |
| 2012/0216705 A1 | 8/2012 | Rogers et al. |
| 2012/0220513 A1 | 8/2012 | Allesen-Holm et al. |
| 2012/0231510 A1 | 9/2012 | Rao et al. |
| 2012/0237983 A1 | 9/2012 | Harlick |
| 2012/0237984 A1 | 9/2012 | Medoff |
| 2012/0238785 A1 | 9/2012 | Zhou et al. |
| 2012/0245336 A1 | 9/2012 | Daly et al. |
| 2012/0252085 A1 | 10/2012 | Edwards et al. |
| 2012/0264107 A1 | 10/2012 | Contag |
| 2012/0266328 A1 | 10/2012 | Gray et al. |
| 2012/0266329 A1 | 10/2012 | Mathur et al. |
| 2012/0270270 A1 | 10/2012 | Goedegebuur et al. |
| 2012/0270278 A1 | 10/2012 | Dhawan et al. |
| 2012/0270289 A1 | 10/2012 | Jeffries et al. |
| 2012/0270298 A1 | 10/2012 | Day et al. |
| 2012/0273338 A1 | 11/2012 | Lee et al. |

(56) References Cited

U.S. PATENT DOCUMENTS

| | | | |
|---|---|---|---|
| 2012/0273339 A1 | 11/2012 | Lee et al. |
| 2012/0276594 A1 | 11/2012 | Voladri et al. |
| 2012/0276595 A1 | 11/2012 | Cascao-Pereira et al. |
| 2012/0277480 A1 | 11/2012 | Lee et al. |
| 2012/0277481 A1 | 11/2012 | Warner et al. |
| 2012/0277482 A1 | 11/2012 | Lee et al. |
| 2012/0277483 A1 | 11/2012 | Horton et al. |
| 2012/0277485 A1 | 11/2012 | Lee et al. |
| 2012/0277486 A1 | 11/2012 | Warner et al. |
| 2012/0277487 A1 | 11/2012 | Lee et al. |
| 2012/0277488 A1 | 11/2012 | Horton et al. |
| 2012/0277489 A1 | 11/2012 | Scates et al. |
| 2012/0277490 A1 | 11/2012 | Lee et al. |
| 2012/0277491 A1 | 11/2012 | Warner et al. |
| 2012/0282239 A1 | 11/2012 | Kensch |
| 2012/0282664 A1 | 11/2012 | Kondo et al. |
| 2012/0282666 A1 | 11/2012 | Noda et al. |
| 2012/0283164 A1 | 11/2012 | Svendsen et al. |
| 2012/0283493 A1 | 11/2012 | Olson et al. |
| 2012/0289450 A1 | 11/2012 | Andersen et al. |
| 2012/0289607 A1 | 11/2012 | Xiong et al. |
| 2012/0291160 A1 | 11/2012 | Raab |
| 2012/0301944 A1 | 11/2012 | Dunn-Coleman et al. |
| 2012/0309060 A1 | 12/2012 | Medoff |
| 2012/0315683 A1 | 12/2012 | Mosier et al. |
| 2012/0316330 A1 | 12/2012 | Zhu et al. |
| 2012/0316376 A1 | 12/2012 | Medoff |
| 2012/0321581 A1 | 12/2012 | DiCosimo et al. |
| 2012/0322078 A1 | 12/2012 | Mcbride et al. |
| 2012/0322117 A1 | 12/2012 | Anton et al. |
| 2012/0322121 A1 | 12/2012 | Mosier et al. |
| 2012/0323049 A1 | 12/2012 | Lee et al. |
| 2012/0323050 A1 | 12/2012 | Lee et al. |
| 2012/0325203 A1 | 12/2012 | Griffin et al. |
| 2012/0329096 A1 | 12/2012 | Foody et al. |
| 2012/0329100 A1 | 12/2012 | Uraki et al. |
| 2012/0329104 A1 | 12/2012 | Kim et al. |
| 2013/0011886 A1 | 1/2013 | Tolan et al. |
| 2013/0011887 A1 | 1/2013 | Dayton et al. |
| 2013/0011895 A1 | 1/2013 | Medoff et al. |
| 2013/0012424 A1 | 1/2013 | Glad et al. |
| 2013/0014293 A1 | 1/2013 | Lin et al. |
| 2013/0023608 A1 | 1/2013 | Kellett et al. |
| 2013/0029382 A1 | 1/2013 | Steffens et al. |
| 2013/0030215 A1 | 1/2013 | Bui et al. |
| 2013/0032466 A1 | 2/2013 | Lee et al. |
| 2013/0034888 A1 | 2/2013 | Aurora et al. |
| 2013/0034891 A1 | 2/2013 | Fanselow et al. |
| 2013/0035516 A1 | 2/2013 | Orosco et al. |
| 2013/0035518 A1 | 2/2013 | Lee et al. |
| 2013/0035519 A1 | 2/2013 | Lee et al. |
| 2013/0035520 A1 | 2/2013 | Jevtic et al. |
| 2013/0035521 A1 | 2/2013 | Orosco et al. |
| 2013/0035522 A1 | 2/2013 | Orosco et al. |
| 2013/0035523 A1 | 2/2013 | Lee et al. |
| 2013/0035524 A1 | 2/2013 | Orosco et al. |
| 2013/0035525 A1 | 2/2013 | Johnston et al. |
| 2013/0040352 A1 | 2/2013 | McDaniel et al. |
| 2013/0045891 A1 | 2/2013 | Beck et al. |
| 2013/0046032 A1 | 2/2013 | Scates et al. |
| 2013/0046119 A1 | 2/2013 | Scates et al. |
| 2013/0046120 A1 | 2/2013 | Zink et al. |
| 2013/0052693 A1 | 2/2013 | Baidyaroy et al. |
| 2013/0052694 A1 | 2/2013 | Montalibet et al. |
| 2013/0052698 A1 | 2/2013 | Yang et al. |
| 2013/0052713 A1 | 2/2013 | Yang et al. |
| 2013/0060070 A1 | 3/2013 | Huber et al. |
| 2013/0065270 A1 | 3/2013 | Bell et al. |

OTHER PUBLICATIONS

Jackson et al. (1997) A Laboratory Guide to Glycoconjugate Analysis., only p. 71.*

Decker et al., Automated Filter Paper Assay for Determination of Cellulase Activity., Applied Biochemistry and Biotechnology (2003), vol. 107, pp. 689-703.*

Gronfors (2010) Thesis, Use of fillers in paper and paperboard grades.*

Kang et al. Enhanced Ethanol Production From De-Ashed Paper Sludge by Simultaneous Saccharification and Fermentation and Simultaneous Saccharification and Co-Fermentation., BioResources (2011), vol. 6(4), pp. 3791-3808.*

Cui et al. Effect of Cellobiase and surfactant supplementation on the Enzymatic Hydrolysis of Pretreated Wheat Straw, BioResources (2011), vol. 6(4), pp. 3850-3858.*

Arvelakis et al. Simultaneous Thermal Analysis (STA) on Ash from High-Alkali Biomass., Energy & Fuels (2004), vol. 18, pp. 1066-1076.*

Tschirner et al. Recycling of Chemical Pulp From Wheat Straw and Corn Stover., BioResources (2007), vol. 2(4), pp. 536-543.*

Chemicool (last viewed on Dec. 1, 2016).*

Robertson (2012), Food Packaging. Principles and Practice, Third Edition, CRC Press, p. 258.*

Wang, Lei, Richard Templer, and Richard J. Murphy. "A Life Cycle Assessment (LCA) comparison of three management options for waste papers: bioethanol production, recycling and incineration with energy recovery." Bioresource Technology (2012).

Kang, Li, Wei Wang, and Yoon Y. Lee. "Bioconversion of kraft paper mill sludges to ethanol by SSF and SSCF." Applied biochemistry and biotechnology 161.1 (2010): 53-66.

Pan, Xuejun, et al. "Biorefining of softwoods using ethanol organosolv pulping: Preliminary evaluation of process streams for manufacture of fuel—grade ethanol and co—products." Biotechnology and Bioengineering 90.4 (2005): 473-481.

Lark, Nicole, et al. "Production of ethanol from recycled paper sludge using cellulase and yeast, Kluveromyces marxianus" Biomass and Bioenergy 12.2 (1997): 135-143.

Fan, Zhiliang, et al. "Conversion of paper sludge to ethanol in a semicontinuous solids-fed reactor." Bioprocess and biosystems engineering 26.2 (2003): 93-101.

Jeffries, Thomas W., and Richard Schartman. "Bioconversion of secondary fiber fines to ethanol using counter-current enzymatic saccharification and co-fermentation." Applied biochemistry and biotechnology 78.1 (1999): 435-444.

Jin, Yongcan, et al. "Green liquor pretreatment of mixed hardwood for ethanol production in a repurposed kraft pulp mill." Journal of Wood Chemistry and Technology 30.1 (2010): 86-104.

Fan, Zhiliang, and Lee R. Lynd. "Conversion of paper sludge to ethanol, II: process design and economic analysis." Bioprocess and biosystems engineering 30.1 (2007): 35-45.

Da Silva, Roberto, Dong K. Yim, and Yong K. Park. "Application of thermostable xylanases from Humicola sp. for pulp improvement." Journal of fermentation and bioengineering 77.1 (1994): 109-111.

Hu, Gang, John A. Heitmann, and Orlando J. Rojas. "Feedstock pretreatment strategies for producing ethanol from wood, bark, and forest residues." BioResources 3.1 (2008): 270-294.

Saha, Badal C. "Hemicellulose bioconversion." Journal of industrial microbiology & biotechnology 30.5 (2003): 279-291.

Gáspár, Melinda, Gergely Kalman, and Kati Reczey. "Corn fiber as a raw material for hemicellulose and ethanol production." Process Biochemistry 42.7 (2007): 1135-1139.

Zhang, Jiayi, and Lee R. Lynd. "Ethanol production from paper sludge by simultaneous saccharification and co-fermentation using recombinant xylose—fermenting microorganisms." Biotechnology and bioengineering 107.2 (2010): 235-244.

Zhang, Yi—Heng Percival, and Lee R. Lynd. "Toward an aggregated understanding of enzymatic hydrolysis of cellulose: noncomplexed cellulase systems." Biotechnology and bioengineering 88.7 (2004): 797-824.

Fan, L. T., Yong—Hyun Lee, and David H. Beardmore. "Mechanism of the enzymatic hydrolysis of cellulose: effects of major structural features of cellulose on enzymatic hydrolysis." Biotechnology and Bioengineering 22.1 (1980): 177-199.

(56) References Cited

OTHER PUBLICATIONS

Mandels, Mary, Lloyd Hontz, and John Nystrom. "Enzymatic hydrolysis of waste cellulose." Biotechnology and Bioengineering 16.11 (2004): 1471-1493.

Philippidis, George P., Tammy K. Smith, and Charles E. Wyman. "Study of the enzymatic hydrolysis of cellulose for production of fuel ethanol by the simultaneous saccharification and fermentation process." Biotechnology and bioengineering 41.9 (1993): 846-853.

Pääkkö, M., et al. "Enzymatic hydrolysis combined with mechanical shearing and high-pressure homogenization for nanoscale cellulose fibrils and strong gels." Biomacromolecules 8.6 (2007): 1934-1941.

Yang, Bin, and Charles E. Wyman. "BSA treatment to enhance enzymatic hydrolysis of cellulose in lignin containing substrates." Biotechnology and Bioengineering 94.4 (2006): 611-617.

Sun, Ye, and Jiayang Cheng. "Hydrolysis of lignocellulosic materials for ethanol production: a review." Bioresource technology 83.1 (2002): 1-11.

Saddler, J. N., et al. "Enzymatic hydrolysis of cellulose and various pretreated wood fractions." Biotechnology and bioengineering 24.6 (1982): 1389-1402.

Khodaverdi, Mahdi, et al. "Kinetic modeling of rapid enzymatic hydrolysis of crystalline cellulose after pretreatment by NMMO." Journal of industrial microbiology & biotechnology (2012): 1-10.

Obama, Patrick, et al. "Combination of enzymatic hydrolysis and ethanol organosolv pretreatments: Effect on lignin structures, delignification yields and cellulose-to-glucose conversion." Bioresource Technology (2012).

Wiman, Magnus, et al. "Cellulose accessibility determines the rate of enzymatic hydrolysis of steam-pretreated spruce." Bioresource Technology (2012).

Elliston, Adam, et al. "High concentrations of cellulosic ethanol achieved by fed batch semi simultaneous saccharification and fermentation of waste-paper." Bioresource Technology (2013).

Kinnarinen, Teemu, et al. "Effect of mixing on enzymatic hydrolysis of cardboard waste: Saccharification yield and subsequent separation of the solid residue using a pressure filter" Bioresource technology (2012).

Wang, Lei, Richard Templer, and Richard J. Murphy. "High-solids loading enzymatic hydrolysis of waste papers for biofuel production." Applied Energy (2012).

Li, Sujing, Xiaonan Zhang, and John M. Andresen. "Production of fermentable sugars from enzymatic hydrolysis of pretreated municipal solid waste after autoclave process." Fuel 92.1 (2012): 84-88.

Dubey, Alok Kumar, et al. "Bioethanol production from waste paper acid pretreated hydrolyzate with xylose fermenting< i> Pichia stipitis</i>." Carbohydrate Polymers (2012).

Kinnarinen, Teemu, et al. "Solid—liquid separation of hydrolysates obtained from enzymatic hydrolysis of cardboard waste." Industrial Crops and Products 38 (2012): 72-80.

Kang, Li. Bioconversion of Pulp and Paper Mills Sludge and Prehydrolysate Stream into Ethanol and Cellulase Enzyme. Diss. Auburn University, 2011.

Das, Arpan, et al. "Production of Cellulolytic Enzymes by Aspergillus fumigatus ABK9 in Wheat Bran-Rice Straw Mixed Substrate and Use of Cocktail Enzymes for Deinking of Waste Office Paper Pulp." Bioresource technology (2012).

Chen, Hui, et al. "Enzymatic Hydrolysis of Recovered Office Printing Paper with Low Enzyme Dosages to Produce Fermentable Sugars." Applied biochemistry and biotechnology (2012): 1-16.

Yan, Shoubao, et al. "Fed batch enzymatic saccharification of food waste improves the sugar concentration in the hydrolysates and eventually the ethanol fermentation by Saccharomyces cerevisiae H058." Brazilian Archives of Biology and Technology 55.2 (2012): 183-192.

Arora, Anju, et al. "Effect of Formic Acid and Furfural on the Enzymatic Hydrolysis of Cellulose Powder and Dilute Acid-Pretreated Poplar Hydrolysates." ACS Sustainable Chemistry & Engineering 1.1 (2012): 23-28.

Wang, Lei, et al. "Technology performance and economic feasibility of bioethanol production from various waste papers." Energy & Environmental Science 5.2 (2012): 5717-5730.

Vazana, Yael, et al. "Designer Cellulosomes for Enhanced Hydrolysis of Cellulosic Substrates." Cellulases (2012): 429.

Van Dyk, J. S., and B. I. Pletschke. "A review of lignocellulose bioconversion using enzymatic hydrolysis and synergistic cooperation between enzymes—Factors affecting enzymes, conversion and synergy." Biotechnology Advances (2012).

Menind, A., et al. "Pretreatment and usage of pulp and paper industry residues for fuels production and their energetic potential." International Scientific Conference Biosystems Engineering, Tartu, Estonia, May 10-11, 2012.. vol. 10. No. Special Issue I. Estonian Research Institute of Agriculture, 2012.

Han, Lirong, et al. "Alkali pretreated of wheat straw and its enzymatic hydrolysis." Brazilian Journal of Microbiology 43.1 (2012): 53-61.

Holm, Jana, et al. "Pretreatment of fibre sludge in ionic liquids followed by enzyme and acid catalysed hydrolysis." Catalysis Today (2012).

Van Heiningen, Adriaan. "Converting a kraft pulp mill into an integrated forest products biorefinery." Annual Meeting-Pulp and Paper Technical Association of Canada. vol. 92. No. C. Pulp and Paper Technical Association of Canada; 1999, 2006.

Zhu, J. Y., and X. J. Pan. "Woody biomass pretreatment for cellulosic ethanol production: technology and energy consumption evaluation." Bioresource technology 101.13 (2010): 4992-5002.

Pérez, J., et al. "Biodegradation and biological treatments of cellulose, hemicellulose and lignin: an overview." International Microbiology 5.2 (2002): 53-63.

Kadam, Kiran L., Chim Y. Chin, and Lawrence W. Brown. "Flexible biorefinery for producing fermentation sugars, lignin and pulp from corn stover." Journal of industrial microbiology & biotechnology 35.5 (2008): 331-341.

Kuhad, Ramesh Chander, and Ajay Singh. "Lignocellulose biotechnology: current and future prospects." Critical Reviews in Biotechnology 13.2 (1993): 151-172.

Lawford, Hugh G., and Joyce D. Rousseau. "Production of ethanol from pulp mill hardwood and softwood spent sulfite liquors by genetically engineered E. coli." Applied biochemistry and biotechnology 39.1 (1993): 667-685.

Burchhardt, G., and L. O. Ingram. "Conversion of xylan to ethanol by ethanologenic strains of Escherichia coli and Klebsiella oxytoca." Applied and environmental microbiology 58.4 (1992): 1128-1133.

Zhu, J. Y., Ronald Sabo, and Xiaolin Luo. "Integrated production of nano-fibrillated cellulose and cellulosic biofuel (ethanol) by enzymatic fractionation of wood fibers." Green Chemistry 13.5 (2011): 1339-1344.

Ichiura, Hideaki, Takuhiro Nakatani, and Yoshito Ohtani. "Separation of pulp and inorganic materials from paper sludge using ionic liquid and centrifugation." Chemical Engineering Journal 173.1 (2011): 129-134.

López-Contreras, Ana M., et al. "Utilisation of saccharides in extruded domestic organic waste by Clostridium acetobutylicum ATCC 824 for production of acetone, butanol and ethanol." Applied microbiology and biotechnology 54.2 (2000): 162-167.

Zhang, Xiao, et al. "High consistency enzymatic hydrolysis of hardwood substrates." Bioresource technology 100.23 (2009): 5890-5897.

Kirk, T. Kent, T. W. Jeffries, and George F. Leatham. "Biotechnology: applications and implications for the pulp and paper industry." Tappi J 66.5 (1983): 45-51.

Yamashita, Yuya, et al. "Ethanol production from paper sludge by immobilized Zymomonas mobilis." Biochemical Engineering Journal 42.3 (2008): 314-319.

Lee, Sang-Mok, Jianqiang Lin, and Yoon-Mo Koo. "Hydrolysis of Paper Sludge Using Mixed Cellulase System: Enzymtic Hydrolysis of Paper Sludge." ACS Symposium Series. vol. 830. Washington, DC; American Chemical Society; 1999, 2002.

Kang, Li, et al. "Enhanced Ethanol Production from De-Ashed Paper Sludge by Simultaneous Saccharification and Fermentation

(56) References Cited

OTHER PUBLICATIONS and Simultaneous Saccharification and Co-Fermentation." BioResources 6.4 (2011): 3791-3808.

Prasetyo, Joni, and Enoch Y. Park. "Waste paper sludge as a potential biomass for bio-ethanol production." Korean Journal of Chemical Engineering 30.2 (2013): 253-261.

Shammas, Nazih K., Lawrence K. Wang, and Mark Landin. "Treatment of Paper Mill Whitewater, Recycling and Recovery of Raw Materials." Flotation Technology (2010): 221-268.

* cited by examiner

HYDROLYSIS OF CELLULOSIC FINES IN PRIMARY CLARIFIED SLUDGE OF PAPER MILLS AND THE ADDITION OF A SURFACTANT TO INCREASE THE YIELD

CROSS REFERENCE TO RELATED APPLICATION

The present application is a non-provisional of, and claims benefit of priority under 35 U.S.C. §119(e) from U.S. Provisional Patent Application Ser. No. 61/792,793, filed Mar. 15, 2014, the entirety of which is expressly incorporated herein by reference.

GOVERNMENT RIGHTS

Not Applicable

FIELD OF THE INVENTION

This invention relates to processing of cellulosic solid waste from paper related industries for extraction of fermentable sugars.

BACKGROUND OF THE INVENTION

Lignocellulosic materials are excellent sources for energy products, platform chemicals and bioplastics. Sugars produced by the degradation of carbohydrate polymers can be fermented into ethanol and butanol as energy sources. Sugars and cellulose degradation compounds can serve as platform chemicals in the production of bulk chemicals and they can also be used as feedstocks for microbial production of plastics such as polyhydrolxyalkanoates.

See, U.S. Pat. Nos. 8,395,023; 8,394,617; 8,394,616; 8,389,260; 8,389,259; 8,389,258; 8,389,257; 8,389,256; 8,389,255; 8,389,254; 8,377,659; 8,372,598; 8,367,819; 8,362,322; 8,361,767; 8,361,762; 8,357,523; 8,354,263; 8,343,747; 8,334,430; 8,328,947; 8,323,947; 8,318,461; 8,317,975; 8,309,328; 8,298,802; 8,298,799; 8,298,795; 8,293,508; 8,288,148; 8,288,144; 8,283,150; 8,278,260; 8,278,079; 8,273,559; 8,257,959; 8,247,647; 8,247,203; 8,241,881; 8,241,461; 8,236,551; 8,236,546; 8,236,542; 8,236,535; 8,232,080; 8,227,236; 8,217,227; 8,216,815; 8,212,087; 8,206,964; 8,206,963; 8,202,831; 8,202,709; 8,192,968; 8,178,336; 8,173,410; 8,168,038; 8,158,397; 8,148,579; 8,148,133; 8,143,480; 8,143,050; 8,142,620; 8,133,711; 8,119,385; 8,114,974; 8,114,655; 8,101,398; 8,101,393; 8,101,024; 8,097,445; 8,097,442; 8,093,037; 8,092,647; 8,083,906; 8,080,398; 8,071,351; 8,071,349; 8,067,222; 8,063,201; 8,061,362; 8,043,839; 8,043,837; 8,034,592; 8,030,050; 8,017,820; 8,017,372; 8,008,056; 7,998,711; 7,993,898; 7,993,890; 7,993,463; 7,981,646; 7,981,644; 7,981,643; 7,977,450; 7,972,832; 7,967,904; 7,964,383; 7,960,528; 7,960,160; 7,960,151; 7,960,148; 7,960,146; 7,954,734; 7,951,571; 7,951,570; 7,947,813; 7,946,295; 7,943,363; 7,939,488; 7,932,072; 7,932,065; 7,931,784; 7,927,854; 7,923,236; 7,923,235; 7,923,233; 7,910,347; 7,906,704; 7,901,511; 7,887,862; 7,875,292; 7,867,745; 7,838,666; 7,829,732; 7,816,581; 7,811,799; 7,810,507; 7,807,434; 7,803,601; 7,786,351; 7,786,350; 7,785,854; 7,754,457; 7,741,089; 7,732,173; 7,727,754; 7,727,746; 7,723,568; 7,709,697; 7,682,811; 7,670,813; 7,659,099; 7,651,582; 7,642,079; 7,632,479; 7,611,882; 7,601,529; 7,592,434; 7,592,163; 7,585,652; 7,582,462; 7,547,534; 7,527,959; 7,504,120; 7,503,981; 7,459,299; 7,452,707; 7,449,550; 7,449,319; 7,431,942; 7,407,788; 7,399,855; 7,399,485; 7,381,553; 7,361,736; 7,351,573; 7,351,568; 7,344,871; 7,320,886; 7,273,742; 7,226,773; 7,226,772; 7,198,925; 7,183,093; 7,172,891; 7,144,716; 7,083,673; 7,070,805; 7,067,303; 7,056,721; 7,049,125; 7,048,952; 7,045,332; 7,045,331; 7,033,811; 7,005,289; 6,982,159; 6,911,565; 6,908,995; 6,894,199; 6,878,199; 6,855,531; 6,818,434; 6,815,192; 6,768,001; 6,713,460; 6,630,340; 6,620,605; 6,566,114; 6,555,335; 6,555,228; 6,500,658; 6,451,063; 6,444,653; 6,420,165; 6,399,351; 6,387,690; 6,333,181; 6,328,994; 6,268,197; 6,268,196; 6,228,630; 6,207,436; 6,197,564; 6,174,700; 6,153,413; 6,140,105; 6,132,998; 6,130,076; 6,110,712; 6,080,567; 6,074,856; 6,069,136; 6,048,715; 6,017,740; 6,013,490; 6,010,870; 6,008,176; 6,005,141; 6,001,639; 5,989,887; 5,962,278; 5,962,277; 5,908,649; 5,885,819; 5,874,276; 5,871,550; 5,866,392; 5,863,783; 5,861,271; 5,792,630; 5,786,313; 5,770,010; 5,747,082; 5,705,369; 5,693,518; 5,683,911; 5,554,520; 5,518,902; 5,505,950; 5,503,996; 5,487,989; 5,464,832; 5,458,899; 5,437,992; 5,424,417; 5,424,202; 5,416,210; 5,395,623; 5,395,455; 5,391,561; 5,302,592; 5,300,672; 5,292,762; 5,179,127; 5,171,570; 5,170,620; 5,166,390; 5,151,447; 5,149,524; 5,118,681; 5,112,382; 5,102,898; 5,091,399; 5,081,026; 5,059,654; 5,055,308; 5,037,663; 5,023,275; 4,975,459; 4,950,597; 4,851,394; 4,831,127; 4,713,118; 4,694,906; 4,628,029; 4,594,130; 4,540,587; 4,431,675; 4,321,360; 4,321,328; 4,321,278; 4,292,406; 4,275,163; 4,260,685; 4,235,968; 4,058,411; 4,017,642; 3,990,944; Published Patent application Nos. 20130065270; 20130060070; 20130052713; 20130052698; 20130052694; 20130052693; 20130046120; 20130046119; 20130046032; 20130045891; 20130040352; 20130035525; 20130035524; 20130035523; 20130035522; 20130035521; 20130035520; 20130035519; 20130035518; 20130035516; 20130034891; 20130034888; 20130032466; 20130030215; 20130029382; 20130023608; 20130014293; 20130012424; 20130011895; 20130011887; 20130011886; 20120329104; 20120329100; 20120329096; 20120325203; 20120323050; 20120323049; 20120322121; 20120322078; 20120321581; 20120316376; 20120316330; 20120315683; 20120309060; 20120301944; 20120291160; 20120289607; 20120289450; 20120283493; 20120282664; 20120277491; 20120277490; 20120277489; 20120277488; 20120277487; 20120277486; 20120277485; 20120277484; 20120277483; 20120277482; 20120277481; 20120277480; 20120276595; 20120276594; 20120273339; 20120273338; 20120270298; 20120270289; 20120270278; 20120270270; 20120266329; 20120266328; 20120264107; 20120252085; 20120245336; 20120238785; 20120237984; 20120237983; 20120231510; 20120220513; 20120216705; 20120214209; 20120211184; 20120210467; 20120209034; 20120208235; 20120199299; 20120199298; 20120196338; 20120190840; 20120190076; 20120190054; 20120184020; 20120184007; 20120178975; 20120165562; 20120165517; 20120164709; 20120164696; 20120159840; 20120159839; 20120157725; 20120157721; 20120156754; 20120156741; 20120156162; 20120156161; 20120156160; 20120156159; 20120156158; 20120156157; 20120156156; 20120156155; 20120151827; 20120149949; 20120149077; 20120149065; 20120146468; 20120142886; 20120142068; 20120142065; 20120142046; 20120135500; 20120135499; 20120135489; 20120129696; 20120129229; 20120111321; 20120108798; 20120107892; 20120107888; 20120107887; 20120107881; 20120107880; 20120101250; 20120100587; 20120100045; 20120094358; 20120094355; 20120094343; 20120083019; 20120079665; 20120077247; 20120077216; 20120066781; 20120064609; 20120064592; 20120064579; 20120059197; 20120052534; 20120046501; 20120045812; 20120045811; 20120041075; 20120040435; 20120040409;

20120036769; 20120036768; 20120036599; 20120035400; 20120030838; 20120029247; 20120028325; 20120028306; 20120021490; 20120021092; 20120015422; 20120015408; 20120010445; 20120010447; 20120010446; 20120010445; 20120010444; 20120010443; 20120010440; 20120010439; 20120010438; 20120010437; 20120010436; 20120009640; 20120009634; 20120009631; 20120006320; 20120005949; 20120003704; 20120003703; 20120003701; 20110319849; 20110318798; 20110318796; 20110315154; 20110314726; 20110312058; 20110312055; 20110312048; 20110306117; 20110306083; 20110300586; 20110296555; 20110296543; 20110294181; 20110294165; 20110294164; 20110275130; 20110271875; 20110269201; 20110268858; 20110262985; 20110262984; 20110251377; 20110250674; 20110250667; 20110250638; 20110250635; 20110239333; 20110237769; 20110236339; 20110236338; 20110236337; 20110236336; 20110236335; 20110233042; 20110232164; 20110232163; 20110232162; 20110232161; 20110232160; 20110229959; 20110229956; 20110224416; 20110212505; 20110212499; 20110207192; 20110190488; 20110185456; 20110183379; 20110178261; 20110177573; 20110177565; 20110177561; 20110171709; 20110171705; 20110165661; 20110165660; 20110159544; 20110155559; 20110152812; 20110152370; 20110152369; 20110152368; 20110150857; 20110146138; 20110144241; 20110143398; 20110139662; 20110139659; 20110139658; 20110139657; 20110138502; 20110136908; 20110136907; 20110136196; 20110136174; 20110130488; 20110129887; 20110129881; 20110129880; 20110125118; 20110124074; 20110124058; 20110117619; 20110117067; 20110111456; 20110100359; 20110097786; 20110095111; 20110093965; 20110091950; 20110091940; 20110086410; 20110086408; 20110081697; 20110081412; 20110081336; 20110081335; 20110076743; 20110065910; 20110061666; 20110053245; 20110046422; 20110045544; 20110040058; 20110039320; 20110039317; 20110039309; 20110039308; 20110035839; 20110035838; 20110033391; 20110028672; 20110027837; 20110027346; 20110020874; 20110016545; 20110014672; 20110003345; 20110003341; 20110000125; 20100330633; 20100319862; 20100317087; 20100317059; 20100312028; 20100304440; 20100304439; 20100298612; 20100297721; 20100297704; 20100287826; 20100285534; 20100279361; 20100279354; 20100273214; 20100268000; 20100267110; 20100263264; 20100240128; 20100223694; 20100221819; 20100221784; 20100216200; 20100212091; 20100196978; 20100196977; 20100189706; 20100184178; 20100184175; 20100179315; 20100167371; 20100167370; 20100160201; 20100159566; 20100159553; 20100159510; 20100151551; 20100151547; 20100151546; 20100144584; 20100143998; 20100137647; 20100136661; 20100136113; 20100129835; 20100124583; 20100113846; 20100112242; 20100108567; 20100107342; 20100105114; 20100101605; 20100099640; 20100095390; 20100087687; 20100086978; 20100068790; 20100068768; 20100056774; 20100055753; 20100055747; 20100048964; 20100048417; 20100041104; 20100035320; 20100031398; 20100028966; 20100021988; 20100011456; 20100003733; 20100003716; 20100003234; 20090325254; 20090324574; 20090312537; 20090312221; 20090311752; 20090298149; 20090297495; 20090286295; 20090286294; 20090280105; 20090258172; 20090247448; 20090235388; 20090234142; 20090233335; 20090226979; 20090224086; 20090221051; 20090220480; 20090217569; 20090209009; 20090203102; 20090202675; 20090198046; 20090194243; 20090181433; 20090181126; 20090176292; 20090172838; 20090170747; 20090170181; 20090163397; 20090155238; 20090142848; 20090136476; 20090099079; 20090098266; 20090093028; 20090081762; 20090075336; 20090070898; 20090068714; 20090061490; 20090042266; 20090042259; 20090038023; 20090036648; 20090035826; 20090025739; 20090025738; 20090017512; 20090013434; 20090005532; 20090004726; 20080311640; 20080305531; 20080293114; 20080293086; 20080292747; 20080292701; 20080274527; 20080261267; 20080254080; 20080248160; 20080241900; 20080233175; 20080229657; 20080229456; 20080227173; 20080206836; 20080202684; 20080201801; 20080193981; 20080176282; 20080145912; 20080138880; 20080113413; 20080102502; 20080095889; 20080085536; 20080085520; 20080076314; 20080076152; 20080070291; 20080064906; 20080056983; 20080034453; 20080029110; 20080020435; 20080009047; 20070298475; 20070254031; 20070219521; 20070213249; 20070207530; 20070202566; 20070199095; 20070192903; 20070178569; 20070173431; 20070172916; 20070149777; 20070148751; 20070148730; 20070141693; 20070141660; 20070118918; 20070118917; 20070113302; 20070113301; 20070105112; 20070094748; 20070092935; 20070092934; 20070089196; 20070089195; 20070089194; 20070089193; 20070089192; 20070089191; 20070089190; 20070089189; 20070089188; 20070089187; 20070089186; 20070089185; 20070089184; 20070087066; 20070083952; 20070083951; 20070083950; 20070083949; 20070083947; 20070079944; 20070072185; 20070059813; 20070036832; 20070031954; 20070011775; 20060281157; 20060275241; 20060259995; 20060258554; 20060255507; 20060235115; 20060211101; 20060210971; 20060205042; 20060200878; 20060188965; 20060182802; 20060166322; 20060165613; 20060154844; 20060154352; 20060141601; 20060135388; 20060110797; 20060104931; 20060089283; 20060084156; 20060068475; 20060057672; 20060046284; 20060035353; 20060018862; 20060003433; 20050277172; 20050272836; 20050244934; 20050244878; 20050221369; 20050214921; 20050210548; 20050125860; 20050120915; 20050100996; 20050070003; 20050054039; 20050037459; 20050009166; 20040266642; 20040259218; 20040231661; 20040210099; 20040203134; 20040157301; 20040121436; 20040102619; 20040067569; 20040053238; 20030225005; 20030216492; 20030203466; 20030203454; 20030180900; 20030125588; 20030119006; 20030114330; 20030113735; 20030113734; 20030113732; 20030097029; 20030092097; 20030087415; 20030082779; 20030054539; 20030054518; 20030054500; 20030032162; 20030032148; 20030032084; 20030022807; 20020193272; 20020164774; 20020160469; 20020156048; 20020142034; 20020045057; 20020012980; 20010044138; 20010010825, each of which is expressly incorporated herein by reference.

See also,

Van Heiningen, Adriaan. "Converting a kraft pulp mill into an integrated forest products biorefinery." *ANNUAL MEETING-PULP AND PAPER TECHNICAL ASSOCIATION OF CANADA*. Vol. 92. No. C. Pulp and Paper Technical Association of Canada; 1999, 2006.

Zhu, J. Y., and X. J. Pan. "Woody biomass pretreatment for cellulosic ethanol production: technology and energy consumption evaluation." *Bioresource technology* 101.13 (2010): 4992-5002.

Pérez, J., et al. "Biodegradation and biological treatments of cellulose, hemicellulose and lignin: an overview." *International Microbiology* 5.2 (2002): 53-63.

Kadam, Kiran L., Chim Y. Chin, and Lawrence W. Brown. "Flexible biorefinery for producing fermentation sugars, lignin and pulp from corn stover." *Journal of industrial microbiology & biotechnology* 35.5 (2008): 331-341.

Kuhad, Ramesh Chander, and Ajay Singh. "Lignocellulose biotechnology: current and future prospects." *Critical Reviews in Biotechnology* 13.2 (1993): 151-172.

Lawford, Hugh G., and Joyce D. Rousseau. "Production of ethanol from pulp mill hardwood and softwood spent sulfite liquors by genetically engineered *E. coli.*" *Applied biochemistry and biotechnology* 39.1 (1993): 667-685.

Burchhardt, G., and L. O. Ingram. "Conversion of xylan to ethanol by ethanologenic strains of *Escherichia coli* and *Klebsiella oxytoca.*" *Applied and environmental microbiology* 58.4 (1992): 1128-1133.

Zhu, J. Y., Ronald Sabo, and Xiaolin Luo. "Integrated production of nano-fibrillated cellulose and cellulosic biofuel (ethanol) by enzymatic fractionation of wood fibers." *Green Chemistry* 13.5 (2011): 1339-1344.

Hoge, William H. "Process for making ethanol and fuel product." U.S. Pat. No. 4,321,328. 23 Mar. 1982.

López-Contreras, Ana M., et al. "Utilisation of saccharides in extruded domestic organic waste by *Clostridium acetobutylicum* ATCC 824 for production of acetone, butanol and ethanol." *Applied microbiology and biotechnology* 54.2 (2000): 162-167.

Zhang, Xiao, et al. "High consistency enzymatic hydrolysis of hardwood substrates." *Bioresource technology* 100.23 (2009): 5890-5897.

Kirk, T. Kent, T. W. Jeffries, and George F. Leatham. "Biotechnology: applications and implications for the pulp and paper industry." *Tappi J* 66.5 (1983): 45-51.

Yamashita, Yuya, et al. "Ethanol production from paper sludge by immobilized *Zymomonas mobilis.*" *Biochemical Engineering Journal* 42.3 (2008): 314-319.

Lee, Sang-Mok, Jianqiang Lin, and Yoon-Mo Koo. "Hydrolysis of Paper Sludge Using Mixed Cellulase System: Enzymtic Hydrolysis of Paper Sludge." *ACS Symposium Series*. Vol. 830. Washington, D.C.; American Chemical Society; 1999, 2002.

Kang, Li, et al. "Enhanced Ethanol Production from De-Ashed Paper Sludge by Simultaneous Saccharification and Fermentation and Simultaneous Saccharification and Co-Fermentation." *BioResources* 6.4 (2011): 3791-3808.

Chen, Hui, et al. "Enzymatic Hydrolysis of Recovered Office Printing Paper with Low Enzyme Dosages to Produce Fermentable Sugars." *Applied biochemistry and biotechnology* (2012): 1-16.

McManigal, Brent Alan. "SYSTEM AND METHOD FOR PRODUCING ETHANOL FROM PAPER MILL SLUDGE." U.S. patent application Ser. No. 11/735,633.

Elliston, Adam, et al. "High concentrations of cellulosic ethanol achieved by fed batch semi simultaneous saccharification and fermentation of waste-paper." *Bioresource Technology* (2013).

Shammas, Nazih K., Lawrence K. Wang, and Mark Landin. "Treatment of Paper Mill Whitewater, Recycling and Recovery of Raw Materials." *Flotation Technology* (2010): 221-268.

Kang, Li. *Bioconversion of Pulp and Paper Mills Sludge and Prehydrolysate Stream into Ethanol and Cellulase Enzyme*. Diss. Auburn University, 2011.

Prasetyo, Joni, and Enoch Y. Park. "Waste paper sludge as a potential biomass for bioethanol production." *Korean Journal of Chemical Engineering* 30.2 (2013): 253-261.

Ichiura, Hideaki, Takuhiro Nakatani, and Yoshito Ohtani. "Separation of pulp and inorganic materials from paper sludge using ionic liquid and centrifugation." *Chemical Engineering Journal* 173.1 (2011): 129-134.

Wang, Lei, Richard Templer, and Richard J. Murphy. "A Life Cycle Assessment (LCA) comparison of three management options for waste papers: bioethanol production, recycling and incineration with energy recovery." *Bioresource Technology* (2012).

Kang, Li, Wei Wang, and Yoon Y. Lee. "Bioconversion of kraft paper mill sludges to ethanol by SSF and SSCF." *Applied biochemistry and biotechnology* 161.1 (2010): 53-66.

Pan, Xuejun, et al. "Biorefining of softwoods using ethanol organosolv pulping: Preliminary evaluation of process streams for manufacture of fuel-grade ethanol and co-products." *Biotechnology and Bioengineering* 90.4 (2005): 473-481.

Lark, Nicole, et al. "Production of ethanol from recycled paper sludge using cellulase and yeast, *Kluveromyces marxianus*" *Biomass and Bioenergy* 12.2 (1997): 135-143.

Fan, Zhiliang, et al. "Conversion of paper sludge to ethanol in a semicontinuous solids-fed reactor." *Bioprocess and biosystems engineering* 26.2 (2003): 93-101.

Jeffries, Thomas W., and Richard Schartman. "Bioconversion of secondary fiber fines to ethanol using countercurrent enzymatic saccharification and co-fermentation." *Applied biochemistry and biotechnology* 78.1 (1999): 435-444.

Jin, Yongcan, et al. "Green liquor pretreatment of mixed hardwood for ethanol production in a repurposed kraft pulp mill." *Journal of Wood Chemistry and Technology* 30.1 (2010): 86-104.

Fan, Zhiliang, and Lee R. Lynd. "Conversion of paper sludge to ethanol, II: process design and economic analysis." *Bioprocess and biosystems engineering* 30.1 (2007): 35-45.

Da Silva, Roberto, Dong K. Yim, and Yong K. Park. "Application of thermostable xylanases from *Humicola* sp. for pulp improvement." *Journal of fermentation and bioengineering* 77.1 (1994): 109-111.

Hu, Gang, John A. Heitmann, and Orlando J. Rojas. "Feedstock pretreatment strategies for producing ethanol from wood, bark, and forest residues." *BioResources* 3.1 (2008): 270-294.

Villavicencio, Eduardo J., and Jose B. Dos Santos. "Process to produce a high quality paper product and an ethanol product from bamboo." U.S. Pat. No. 5,198,074. 30 Mar. 1993.

Gáspár, Melinda, Gergely Kálmán, and Kati Réczey. "Corn fiber as a raw material for hemicellulose and ethanol production." *Process Biochemistry* 42.7 (2007): 1135-1139.

Zhang, Jiayi, and Lee R. Lynd. "Ethanol production from paper sludge by simultaneous saccharification and co-fermentation using recombinant xylose-fermenting microorganisms." *Biotechnology and bioengineering* 107.2 (2010): 235-244.

Saha, Badal C. "Hemicellulose bioconversion." *Journal of industrial microbiology & biotechnology* 30.5 (2003): 279-291.

Each of the foregoing references is expressly incorporated herein by reference it their entirety.

Paper mills, especially those recycling old cardboard containers (OCC) produce large quantities of fiber fragments which pass through into the waste stream. These fines are composed primarily of cellulose and hemicellulose (amorphous short chain polymers of substituted hexoses and pentoses). They are the source of substantial bioburden due to their long time decay in the environment. Since they contribute substantially to the oxygen demand in the effluents, they are typically separated and sent to landfills by the paper mills. Current landfilling costs are nearly $60/ton, and thus disposal costs to the paper mills are to the tune of $1.5 million/year based on typical sludge production at an average size paper mills in NY at 100 tons/day.

These costs are projected to increase substantially in the future due to the pressure on landfill space. Therefore there is an acute need to divert the wastes, perhaps extracting value through products which not only are marketable but also reduce the landfill volumes.

The waste stream from recycled paper mills contains cellulosic fines and also particles of mineral origin, typically clay or calcium carbonate from the fillers and coatings used in the waste paper. The cellulosic fines are easily hydrolyzable by either acid or enzymatic processes. In the enzymatic process, a cocktail of cellulose enzymes acts progressively and sequentially to open up the cellulose crystalline structure and depolymerize it, producing monomeric sugars. The sugars are primarily glucose and certain other common hexoses which are fermentable into ethanol, butanol or other advanced energy products. Microbial fermentation can also lead to bioplastics such as polyhydroxyalkanoates.

A sample set of fines rejected from a recycled paper mill was obtained. The composition is presented in Table 1 below.

Though the properties of sludge differ not only for different mills but also at different times at same mill, Table 1 is exemplary of possible conditions. The pH of sludge varies between 6 and 8. Ash content is very high for recycled papermills. The short fibers (mainly cellulose fibers) go to belt filter and then to screw press. In general, the PCS contains very high levels of dry solids because it is rich in hydrophobic fibers. To summarize, PCS is a mixture of cellulose fibre (40-65% of dry solids), printing inks and mineral components (25-40% dry solids: kaolin, talc and calcium carbonate). Due to high fiber content PCS has large amount of carbon (around 50% C dry solids) and mineral matter (clay and calcium carbonate, 5-25% dry solids).

TABLE 1

|  | Deinking mill[19] | Deinking mill [20] | Recycle mill [22] | Recycle paper mill [22] |
| --- | --- | --- | --- | --- |
| Total Solids % |  |  | 45 | 50.5 |
|  | 42 | 42 |  |  |
| Ash % | 20.2 | 14 | 3 | 2.8 |

SUMMARY OF THE INVENTION

The present technology processes a waste stream comprising cellulosic fines, e.g., from recycled packaging paper mills, into a stream of fermentable sugars. These fermentable sugars may be fermented to yield bioethanol which is of value as a fuel, for production of biodiesel and other alkoxy esters, and/or manufacturers of other products such as bioplastics such as polyhydroxy alkanoates.

According to a preferred embodiment, a process is provided to:

(a) hydrolyze the cellulosic fines found in recycled paper mill waste streams using a commercially available cellulose enzyme formulation;

(b) increase the enzymatic hydrolysis yield by shielding the inert components of the waste stream using a surfactant; and (c) optimize the surfactant with respect to its composition (anionic, non-ionic or cationic) and dosage.

Recycled containerboard and linerboard paper mills reject significant amounts of cellulosic fines into their waste stream which are eventually landfilled at a cost to the manufacturer and also present a load on the environment. However, it is possible to digest the cellulosic portions of the rejects by enzymatic hydrolysis and thus produce sugars in their monomeric forms. The resulting sugar solutions can be fermented into biofuels such as ethanol and butanol, or processed into biomaterials such as polyhydroxy-alkanoates. The enzymes, however, may have a competitive binding affinity for inorganic particulates, resulting in a non-specific absorption of some or all types of enzymes to the particles. Indeed, similar high surface area particles are used in the purification of similar enzymes. Therefore, in the presence of inorganic particles, such as precipitated calcium carbonate (PCC), the activity and bioavailability of the enzymes may be substantially reduced.

It has been found that surfactants are able to coat the inorganic particulates and otherwise reduce binding of the hydrolytic enzymes, leading to a significant increase in activity, thus saving cost and increasing efficiency. It has been found that effective surfactants do not also block binding or biological activity of the enzymes for the cellulosic particles and components of the solution.

Cationic, non-ionic and anionic surfactants were tested at various dosages. A non-ionic surfactant, Tween 80 (polysorbate 80) was better than the tested cationic and anionic surfactants.

The inorganic particles may be separated from the waste stream, and used as animal bedding or the like.

Some investigators have suggested the use of anaerobic fermentation as a means to degrade and make use of the organic components in the waste stream, but due to presence of large amount of calcium carbonate, kaolin and other fillers, they give rise to problems such as scaling of biomass, reactors and pipes, reduced specific methanogenic activity and loss of buffer capacity, and essential nutrients for anaerobic degradation.

According of the present technology, hydrolysis the cellulosic constituent of PCS and screw press sludge and produce high value fermentable sugars, which permit efficient fermentation to ethanol, and also production of plastics and other useful materials.

The present technology avoids use of membranes or separation tanks to separate inhibitors and thus lowers the cost of separation. It also produces bi-products such as low quality fillers that can be sold to recycled paper mills or animal bedding processors. Because both the organic and inorganic components are separated and made available for downstream use, the amount of burden on landfill is substantially reduced.

Commercially available hydrolysis enzymes include Cellic® HTec3, a concentrated hemicellulase that works alone or in combination with Cellic® CTec3 cellulase enzyme from Novozymes (Denmark).

See:

Zhang, Yi-Heng Percival, and Lee R. Lynd. "Toward an aggregated understanding of enzymatic hydrolysis of cellulose: noncomplexed cellulase systems." Biotechnology and bioengineering 88.7 (2004): 797-824;

Fan, L. T., Yong-Hyun Lee, and David H. Beardmore. "Mechanism of the enzymatic hydrolysis of cellulose: effects of major structural features of cellulose on enzymatic hydrolysis." Biotechnology and Bioengineering 22.1 (1980): 177-199;

Mandels, Mary, Lloyd Hontz, and John Nystrom. "Enzymatic hydrolysis of waste cellulose." Biotechnology and Bioengineering 16.11 (2004): 1471-1493;

Philippidis, George P., Tammy K. Smith, and Charles E. Wyman. "Study of the enzymatic hydrolysis of cellulose for production of fuel ethanol by the simultaneous saccharification and fermentation process." Biotechnology and bioengineering 41.9 (1993): 846-853;

Pääkkö, M., et al. "Enzymatic hydrolysis combined with mechanical shearing and high-pressure homogenization for nanoscale cellulose fibrils and strong gels." Biomacromolecules 8.6 (2007): 1934-1941;

Yang, Bin, and Charles E. Wyman. "BSA treatment to enhance enzymatic hydrolysis of cellulose in lignin containing substrates." Biotechnology and Bioengineering 94.4 (2006): 611-617;

Sun, Ye, and Jiayang Cheng. "Hydrolysis of lignocellulosic materials for ethanol production: a review." Bioresource technology 83.1 (2002): 1-11;

Saddler, J. N., et al. "Enzymatic hydrolysis of cellulose and various pretreated wood fractions." Biotechnology and bioengineering 24.6 (1982): 1389-1402;

Khodaverdi, Mandi, et al. "Kinetic modeling of rapid enzymatic hydrolysis of crystalline cellulose after pretreatment by NMMO." Journal of industrial microbiology & biotechnology (2012): 1-10;

Obama, Patrick, et al. "Combination of enzymatic hydrolysis and ethanol organosolv pretreatments: Effect on lignin structures, delignification yields and cellulose-to-glucose conversion." Bioresource Technology (2012);

Wiman, Magnus, et al. "Cellulose accessibility determines the rate of enzymatic hydrolysis of steam-pretreated spruce." Bioresource Technology (2012);

Elliston, Adam, et al. "High concentrations of cellulosic ethanol achieved by fed batch semi simultaneous saccharification and fermentation of waste-paper." Bioresource Technology (2013);

Kinnarinen, Teemu, et al. "Effect of mixing on enzymatic hydrolysis of cardboard waste: Saccharification yield and subsequent separation of the solid residue using a pressure filter." Bioresource technology (2012);

Wang, Lei, Richard Templer, and Richard J. Murphy. "High-solids loading enzymatic hydrolysis of waste papers for biofuel production." Applied Energy (2012);

Li, Sujing, Xiaonan Zhang, and John M. Andresen. "Production of fermentable sugars from enzymatic hydrolysis of pretreated municipal solid waste after autoclave process." Fuel 92.1 (2012): 84-88;

Dubey, Alok Kumar, et al. "Bioethanol production from waste paper acid pretreated hydrolyzate with xylose fermenting *Pichia stipitis*." Carbohydrate Polymers (2012);

Kinnarinen, Teemu, et al. "Solid-liquid separation of hydrolysates obtained from enzymatic hydrolysis of cardboard waste." Industrial Crops and Products 38 (2012): 72-80;

Nørholm, Nanna Dreyer, Jan Larsen, and Frank Krogh Iversen. "Non-pressurised pretreatment, enzymatic hydrolysis and fermentation of waste fractions." U.S. patent application Ser. No. 13/405,262;

Das, Arpan, et al. "Production of Cellulolytic Enzymes by *Aspergillus fumigatus* ABK9 in Wheat Bran-Rice Straw Mixed Substrate and Use of Cocktail Enzymes for Deinking of Waste Office Paper Pulp." Bioresource technology (2012);

Chen, Hui, et al. "Enzymatic Hydrolysis of Recovered Office Printing Paper with Low Enzyme Dosages to Produce Fermentable Sugars." Applied biochemistry and biotechnology (2012): 1-16;

Yan, Shoubao, et al. "Fed batch enzymatic saccharification of food waste improves the sugar concentration in the hydrolysates and eventually the ethanol fermentation by *Saccharomyces cerevisiae* H058." Brazilian Archives of Biology and Technology 55.2 (2012): 183-192;

Arora, Anju, et al. "Effect of Formic Acid and Furfural on the Enzymatic Hydrolysis of Cellulose Powder and Dilute Acid-Pretreated Poplar Hydrolysates." ACS Sustainable Chemistry & Engineering 1.1 (2012): 23-28;

Wang, Lei, et al. "Technology performance and economic feasibility of bioethanol production from various waste papers." Energy & Environmental Science 5.2 (2012): 5717-5730;

Vazana, Yael, et al. "Designer Cellulosomes for Enhanced Hydrolysis of Cellulosic Substrates." Cellulases (2012): 429;

Van Dyk, J. S., and B. I. Pletschke. "A review of lignocellulose bioconversion using enzymatic hydrolysis and synergistic cooperation between enzymes-Factors affecting enzymes, conversion and synergy." Biotechnology Advances (2012);

Menind, A., et al. "Pretreatment and usage of pulp and paper industry residues for fuels production and their energetic potential." International Scientific Conference Biosystems Engineering, Tartu, Estonia, 10-11 May 2012. Vol. 10. No. Special Issue I. Estonian Research Institute of Agriculture, 2012;

Han, Lirong, et al. "Alkali pretreated of wheat straw and its enzymatic hydrolysis." Brazilian Journal of Microbiology 43.1 (2012): 53-61;

Holm, Jana, et al. "Pretreatment of fibre sludge in ionic liquids followed by enzyme and acid catalysed hydrolysis." Catalysis Today (2012), each of which is expressly incorporated herein by reference.

See also, US Pub. Pat. Appl. 20120329096; 20120322117; 20120283164; 20120282666; 20120282239; 20120184020; 20120184007; 20120171732; 20120115192; 20120097194; 20120094340; 20110306101; 20110306100; 20110300585; 20110275118; 20110250646; 20110229959; 20110224416; 20110201093; 20110195481; 20110183396; 20110165661; 20110165660; 20110146142; 20110129886; 20110117067; 20110039318; 20100304420; 20100291653; 20100279354; 20100221819; 20100199548; 20100196981; 20100189706; 20100075404; 20100071259; 20100068768; 20100003733; 20090318571; 20090317864; 20090298149; 20090209009; 20090170174; 20090137438; 20090056707; 20090056201; 20090053800; 20090053777; 20090050134; 20090004714; 20080227182; 20080227161; 20080193992; 20080102502; 20080064064; 20070241306; 20070227971; 20070221552; 20070218541; 20070207939; 20070199903; 20070175825; 20070072185; 20070037259; 20070031953; 20070031919; 20070031918; 20060246563; 20060154352; 20050244934; 20050148056; 20050129643; 20050118130; 20050075497; 20030211958; 20030203466; 20030022347; 20030013172; 20020195213; 20020164731; and U.S. Pat. Nos. 8,338,139; 8,318,461; 8,309,331; 8,304,219; 8,287,732; 8,273,181; 8,263,368; 8,247,203; 8,227,236; 8,222,010; 8,202,709; 8,187,860; 8,114,974; 8,105,398; 8,093,037; 8,053,566; 7,998,713; 7,960,153; 7,932,063; 7,910,338; 7,846,705; 7,819,976; 7,807,419; 7,781,191; 7,727,746; 7,670,813; 7,625,728; 7,585,652; 7,566,561; 7,344,876; 7,183,093; 7,109,005; 6,942,754; 6,663,780; 6,623,948; 6,566,114; 6,528,298; 6,399,351; 6,361,989; 6,309,871; 6,074,856; 5,888,806; 5,736,032; 5,733,758; 5,589,164; 5,587,157; and 5,352,444, each of which is expressly incorporated herein by reference in its entirety.

DETAILED DESCRIPTION OF THE PREFERRED EMBODIMENTS

Hydrolysis experiments were conducted on two different feedstocks. The first was a simulated waste feedstock, consisting of a sample of unbleached kraft softwood pulp (UBSWKP) that is typical of repulped old corrugated containerboard stocks (OCC). The second was an actual reject fines waste stream from a recycled paper board mill. (Supplied by Minimill LLC, Dewitt N.Y. in conjunction with Greenpak LLC, Niagara Falls N.Y.). The reject stream consisted of cellulosic fines (35%) with the remainder as ash-producing constituents. The non-cellulosic portion contains kaolin and precipitated calcium carbonate fillers from the waste paper and smaller amounts of plastic and other residues.

The non-cellulosic portion of the feedstock acts a competitor for enzyme adsorption, and reduces the net yield and productivity of the hydrolysis per unit enzyme reactant. This leads to increased costs and inefficiencies in the hydrolysis process.

Table 2 below shows the enzymatic hydrolysis yields of a sample of waste fines solids from a recycled paper mill. Although the yields are relatively low, an increase would be expected upon routine optimization with respect to enzyme dosages.

The present approach to resolve this problem is to preferentially or selectively cover the inorganic components with a suitable surfactant so that enzyme binding and action is localized to the cellulosic components. For this purpose, cationic, non-ionic and anionic surfactants were tested at different dosages.

Results are shown for the case of the nonionic surfactant. The ionic surfactants tested were not seen as being as effective as the nonionic surfactant.

TABLE 2

Enzymatic hydrolysis of paper mill waste (recycled paper mill, fines from screw press).

| Fines No. | FPU | 3 days surfactant (% on fines) | EH yield | Average | EH yield w/o surfactant | increase | increase based on standard EH |
|---|---|---|---|---|---|---|---|
| 1 | 10 | 3 | 8.1% | | | | |
| 2 | 10 | 3 | 6.2% | 7.2% | 3.1% | 4.1% | 131.0% |
| 3 | 10 | 10 | 6.7% | | | | |
| 4 | 10 | 10 | 4.9% | 5.8% | 3.1% | 2.7% | 86.9% |
| 5 | 25 | 3 | 25.3% | | | | |
| 6 | 25 | 3 | 24.6% | 25.0% | 14.8% | 10.2% | 68.9% |
| 7 | 25 | 10 | 25.4% | | | | |
| 8 | 25 | 10 | 22.8% | 24.1% | 14.8% | 9.3% | 62.9% |

Figure 1:
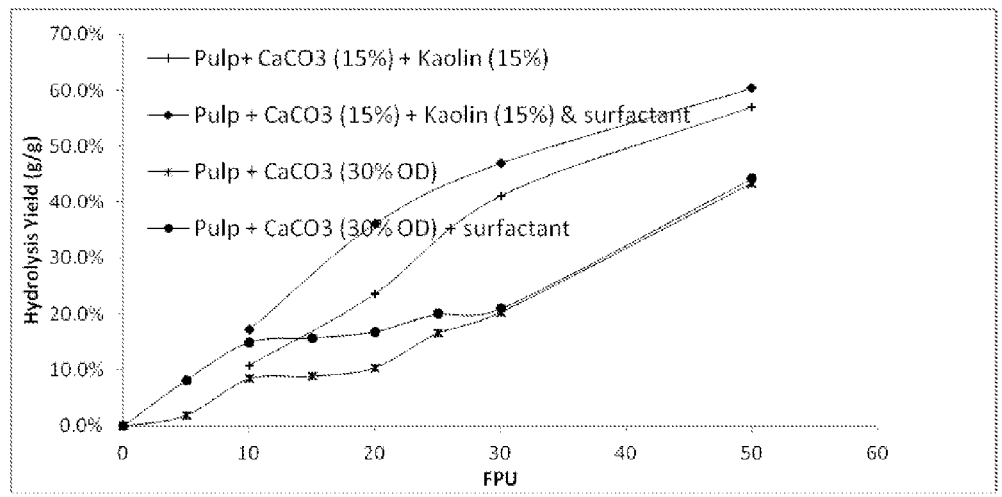
FIG. 1 shows hydrolysis yield of synthetic substrate of varying composition after addition of different concentration of surfactant (Tween80) and enzyme.

A pulp sample (unbleached kraft softwood pulp) was chosen as a model of the OCC pulp. FIG. 1 below shows the hydrolysis yield when a mixture of surfactant and enzyme was applied to this sample mixed with fillers. Hydrolysis yield was defined as the mass of cellulose dissolved (by the action of the enzyme) to the original (oven dry) mass of the sample. Different dosages of the enzyme are represented on the abscissa by FPU. The surfactant added was Tween 80, a polysorbate nonionic carbohydrate based detergent.

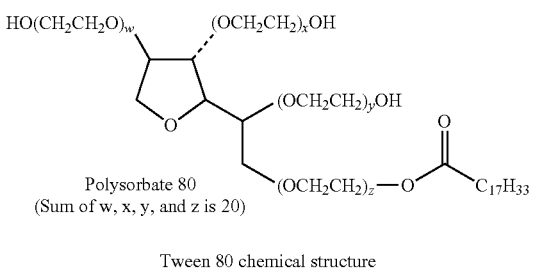

Polysorbate 80
(Sum of w, x, y, and z is 20)

Tween 80 chemical structure

Figure 2:
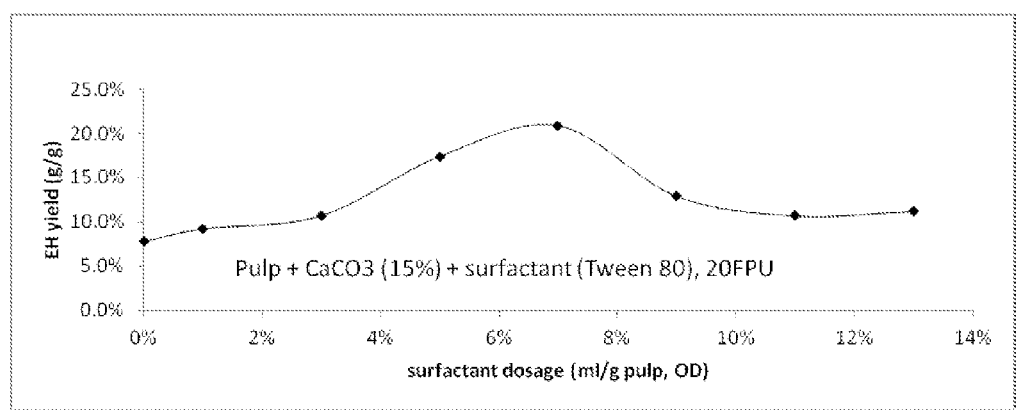
FIG. 2 shows hydrolysis yield of synthetic substrate of Calcium Carbonate (15%) after addition of different concentration of surfactant (Tween80) and enzyme.
Figure 3:
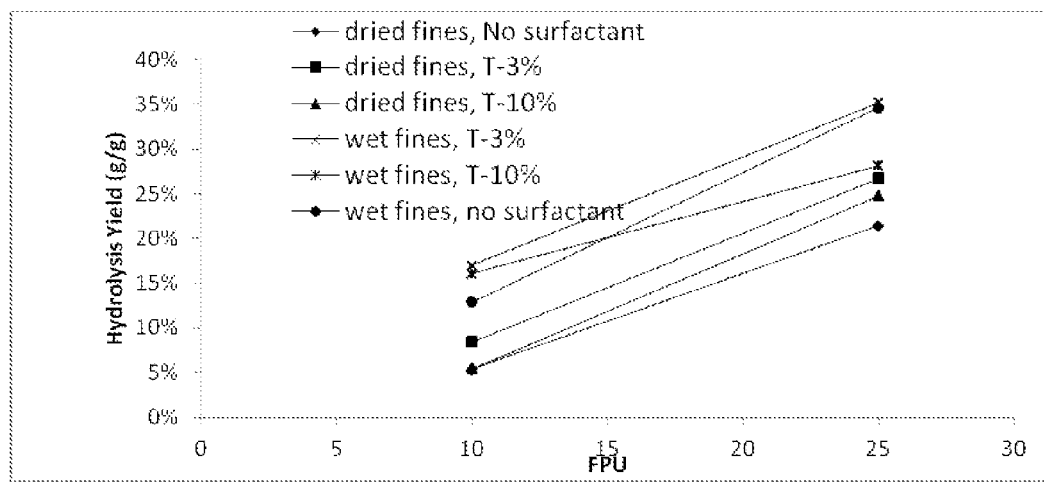
FIG. 3 shows hydrolysis yield of screw press fines with addition of different concentrations of surfactant (Tween 80)

FIG. 1 shows that the addition of the surfactant increases the hydrolysis yield when the enzyme activity is greater than 10 FPUs. The untreated calcium carbonate filler suppresses enzyme hydrolysis, whereas the kaolin filler is more benign to the action of the enzymes. FIG. 2 shows the hydrolysis yield as a function of dosage of the surfactant with enzyme loading chosen as 20 FPUs. The maximum effect surfactant dosage appears to be close to 7% based on the oven dry weight of the biomass. FIG. 3 shows that the hydrolysis yield of mill waste rejects containing fines also increases with the addition of the same nonionic detergent.

The numerous modifications and variations of the present invention are possible in light of the above teachings. It is therefore understood that within the scope of the appended claims, the invention may be practiced otherwise than as specifically described herein.

TABLE 3

Characterization of Fines
Physical characteristics of waste solids from a recycled paper mill.

| Parameter | Value |
|---|---|
| pH | 6.4 |
| Solid content | 52% |
| Particle size | 2.1-3μ |
| Zeta Potential | −9 mV |
| Ash content | % solids |
| Total | 33% |
| Calcium Carbonate | 15% |
| Other fillers and residuals | 18% |

TABLE 4

Properties of Non-ionic surfactant (Polysorbate 80)
Polyelectrolytes:
Tween 80

| Property | Value | Unit |
|---|---|---|
| Charge | Non-ionic | |
| Critical Micelle Concentration | 0.01 | (mM) |
| HLB | 15 | |
| Surface tention | 16 | (dyne/cm) |
| Molecular weight | 1310 | Dalton |

What is claimed is:

1. A method for processing a stream of cellulosic fines rejected from a repulped old corrugated containerboard process for recycling old corrugated containerboard, containing cellulosic fines, and a remainder of 25-65% by oven dry weight of solids being ash-producing components including inorganic particles comprising at least one of calcium carbonate and kaolin, having an affinity for polysaccharide degradative enzymes and reducing the activity of the polysaccharide degradative enzymes in degrading the cellulosic fines, comprising:
adding at least one polysaccharide degradative enzyme to the stream;
adding at least one non-ionic surfactant to the stream in an amount of between 3% and 11% based on the oven dry weight of the stream, adapted to selectively bind surfaces of the at least one of calcium carbonate and kaolin to reduce affinity for the polysaccharide degradative enzymes without inactivating the polysaccharide degradative enzymes, to thereby increase a hydrolytic activity of the at least one polysaccharide degradative enzyme on the cellulosic fines as compared to an absence of the at least one non-ionic surfactant; and
maintaining a solution comprising the cellulosic fines, inorganic particles, at least one non-ionic surfactant, and at least one polysaccharide degradative enzyme for a sufficient period of time to degrade at least a portion of the cellulosic fines into fermentable sugars.

2. The method according to claim 1, further comprising receiving the stream of cellulosic fines as a rejected waste stream from a repulped old corrugated containerboard (OCC) mill.

3. The method according to claim 1, wherein the inorganic particles comprise calcium carbonate.

4. The method according to claim 1, wherein the inorganic particles comprise precipitated calcium carbonate.

5. The method according to claim 1, wherein the inorganic particles comprise kaolin.

6. The method according to claim 1, wherein the at least one polysaccharide degradative enzyme comprises at least one of a cellulase and a hemicellulase.

7. The method according to claim 1, wherein the at least one non-ionic surfactant comprises polysorbate.

8. The method according to claim 1, wherein the at least one non-ionic surfactant comprises polysorbate 80.

9. A method for enzymatically hydrolyzing a mixed stream from a repulped old corrugated containerboard process, comprising cellulosic fines separated from pulp suitable for recycling, containing primarily cellulose and hemicelluloses, and a remainder of 25-65% by oven dry weight of solids as ash-producing constituents including inorganic particles comprising at least one of calcium carbonate and kaolin, having a competitive binding affinity for hydrolytic enzymes, comprising:
adding at least one hydrolytic enzyme to the mixed stream;
adding at least one non-ionic surfactant to the mixed stream in an amount of between 3% and 11% based on the oven dry weight of the mixed stream, to decrease a binding affinity of the at least one hydrolytic enzyme for the inorganic particles and thereby increase a hydrolytic activity of the at least one hydrolytic enzyme as compared to an absence of the at least one non-ionic surfactant on the cellulosic fines; and
hydrolyzing the cellulosic fines with the hydrolytic enzyme.

10. The method according to claim 9, further comprising receiving the mixed stream from a repulped old corrugated containerboard (OCC) mill as rejected material after separation of cellulose fibers for recycling.

11. The method according to claim 9, wherein the inorganic particles comprise calcium carbonate.

12. The method according to claim 9, wherein the inorganic particles comprise precipitated calcium carbonate.

13. The method according to claim 12, wherein the inorganic particles further comprise kaolin.

14. The method according to claim 9, wherein the at least one hydrolytic enzyme comprises at least one of a cellulase and a hemicellulase in an amount of at least 10 FPU (filter paper units).

15. The method according to claim 9, wherein the at least one non-ionic surfactant comprises polysorbate.

16. The method according to claim 9, wherein the at least one non-ionic surfactant comprises polysorbate 80.

17. The method according to claim 9, wherein:
the at least one non-ionic surfactant and the at least one hydrolytic enzyme are added as a mixture to the mixed stream; and
the cellulosic fines are hydrolyzed with the hydrolytic enzyme in an incubator, to produce a solution comprising fermentable sugars from the hydrolyzed cellulosic fines.

18. A method for enzymatically hydrolyzing cellulosic fines in a mixed stream from an old corrugated cardboard recycling process in which the cellulosic fines are separated from pulp for recycling, with at least one hydrolytic enzyme, the mixed stream comprising cellulosic fines containing lignin and a remainder of 25-65% by oven dry weight solids as ash producing inorganic particles comprising at least one of calcium carbonate and kaolin, comprising:
adding at least one non-ionic surfactant to the mixed stream in an amount of between 3% and 10% based on the oven dry weight of the mixed stream, to selectively reduce an affinity of at least one hydrolytic enzyme for the at least one of calcium carbonate and kaolin and to selectively increase a hydrolytic activity with respect to the cellulosic fines of the at least one hydrolytic enzyme as compared to an absence of the at least one non-ionic surfactant;
adding the at least one hydrolytic enzyme to a solution containing the mixed stream of cellulosic fines and inorganic particles and the at least one non-ionic surfactant; and
hydrolyzing the cellulosic fines with the at least one hydrolytic enzyme.

19. The method according to claim 18, wherein the inorganic particles comprise calcium carbonate, the at least one non-ionic surfactant comprises polysorbate and the at least one hydrolytic enzyme comprises at least one of a cellulase and a hemicellulase.

20. The method according to claim 18, wherein the at least one hydrolytic enzyme comprises at least one of a cellulase and a hemicellulase, the inorganic particles having a competitive binding affinity for the at least one hydrolytic enzyme comprise precipitated calcium carbonate, and the at least one non-ionic surfactant comprises a polysorbate surfactant,
further comprising:
separating the inorganic particles from a hydrolysate formed during the hydrolyzing; and
fermenting fermentable sugars in the hydrolysate.

* * * * *